United States Patent

Marui et al.

(10) Patent No.: US 7,541,478 B2
(45) Date of Patent: Jun. 2, 2009

(54) COUMARIN DERIVATIVE AND USE THEREOF

(75) Inventors: Shogo Marui, Osaka (JP); Masaki Ogino, Osaka (JP); Hiroyuki Tawada, Osaka (JP); Osamu Yabe, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 33 days.

(21) Appl. No.: 10/591,561

(22) PCT Filed: Mar. 1, 2005

(86) PCT No.: PCT/JP2005/003838

§ 371 (c)(1),
(2), (4) Date: Aug. 31, 2006

(87) PCT Pub. No.: WO2005/082879

PCT Pub. Date: Sep. 9, 2005

(65) Prior Publication Data

US 2007/0197636 A1     Aug. 23, 2007

(30) Foreign Application Priority Data

Mar. 2, 2004 (JP) .............................. 2004-057920

(51) Int. Cl.
*C07D 311/02* (2006.01)
(52) U.S. Cl. .................. 549/283; 549/285; 549/288
(58) Field of Classification Search .................. 549/283, 549/285, 288
See application file for complete search history.

(56) References Cited

U.S. PATENT DOCUMENTS

| | | | |
|---|---|---|---|
| 5,482,967 A * | 1/1996 | Natsugari et al. | 514/457 |
| 5,700,810 A * | 12/1997 | Natsugari et al. | 514/307 |
| 6,974,806 B2 * | 12/2005 | Terashita et al. | 514/100 |
| 2003/0232809 A1 | 12/2003 | Terashita et al. | |
| 2005/0020634 A1 | 1/2005 | Terashita et al. | |
| 2006/0035865 A1 | 2/2006 | Terashita et al. | |
| 2007/0179154 A1 | 8/2007 | Terashita et al. | |

FOREIGN PATENT DOCUMENTS

| | | |
|---|---|---|
| EP | 0585913 A2 | 9/1993 |
| EP | 1302470 A1 | 4/2003 |
| JP | 2002-255808 A | 9/2002 |
| WO | WO 03/059900 A1 | 7/2003 |

OTHER PUBLICATIONS

International Search Report for PCT/JP2005/003838.
International Preliminary Report on Patentability for PCT/JP2005/003838.

* cited by examiner

*Primary Examiner*—D. Margaret Seaman
*Assistant Examiner*—Nizal S Chandrakumar
(74) *Attorney, Agent, or Firm*—Edwards Angell Palmer & Dodge LLP; David G. Conlin; Mark D. Russett

(57) ABSTRACT

The present invention relates to an alkaline earth metal salt or an organic amine salt of a compound represented by the formula [I]: wherein $R^1$ and $R^2$ are each a hydrogen atom, a halogen atom, or an optionally substituted linear hydrocarbon group; ring A is an optionally further substituted benzene ring; B is an optionally substituted benzene ring; R is a carboxyl group or a linear hydrocarbon group substituted with a carboxyl group and the like.

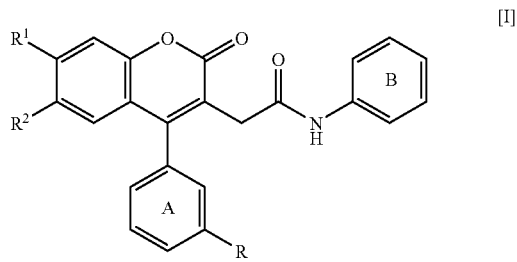

3 Claims, 3 Drawing Sheets

COUMARIN DERIVATIVE AND USE THEREOF

CROSS-REFERENCE TO RELATED APPLICATIONS

This application is the 35 U.S.C. §371 national stage of PCT application PCT/JP2005/003838, filed Mar. 1, 2005, which claims priority to Japanese patent application No. 2004-057920, filed Mar. 2, 2004. The contents of these applications are incorporated herein by reference in their entirety.

TECHNICAL FIELD

The present invention relates to a novel coumarin derivative having lipid-rich plaque regressing activity and/or acyl coenzyme A cholesterol acyl transferase (ACAT) inhibitory activity, which have superior properties as a medicament for preventing or treating coronary syndrome such as myocardial infarction, unstable angina and the like, peripheral artery occlusion, hyperlipemia, cerebral infarction, cerebral apoplexy, arteriosclerosis, atherosclerosis, Alzheimer's disease, or the like.

BACKGROUND ART

Coronary syndrome (for example, unstable angina, myocardial infarction, ischemic sudden death and the like) is caused by rupture of a coronary artery plaque (atheroma) followed by formation of a thrombus and the resultant occlusion of the lumen of a coronary artery. Peripheral artery occlusion is caused by rupture of an artery plaque (atheroma) followed by formation of a thrombus and the resultant occlusion of the lumen of a peripheral artery. These diseases are related closely to the characteristics of a plaque, and a lipid-rich plaque formed by accumulation of a macrophage retaining lipids such as cholesterol extensively onto the inner wall of a blood vessel is believed to cause coronary syndrome and peripheral artery occlusion. A lipid-rich plaque formed at carotid artery or intracerebral vessel is believed to cause cerebral apoplexy or cerebral infarction. Accordingly, regression and removal of a lipid-rich plaque are very important for preventing or treating coronary syndrome such as myocardial infarction and unstable angina as well as peripheral artery occlusion, cerebral apoplexy, or cerebral infarction. Also, since a lipid-rich plaque is observed in a human whose blood cholesterol level is not high and a lipid-rich plaque once formed is difficult to be removed, an agent capable of regressing such a lipid-rich plaque efficiently has been desired.

Before now, it is known that coumarin derivatives of a particular structure have lipid-rich plaque regressing activity and/or ACAT inhibitory activity, and are useful for preventing or treating coronary syndrome and the like (WO02/06264 and WO03/059900).

DISCLOSURE OF INVENTION

The present invention aims at providing novel compounds which are clinically further useful as a medicament for preventing or treating coronary syndrome such as myocardial infarction and unstable angina, as well as peripheral artery occlusion, cerebral apoplexy, or cerebral infarction.

The present inventors found that novel salts of coumarin derivatives having a particular structure possess unexpectedly excellent properties (for example, physicochemical properties such as crystallizability, stability and the like) as well as oral absorbability, regress lipid-rich plaque potently in vivo, and can be extremely superior compounds clinically as an agent for preventing or treating coronary syndrome such as myocardial infarction and unstable angina, as well as peripheral artery occlusion, cerebral apoplexy, cerebral infarction or the like, which resulted in completion of the present invention.

That is, the present invention relates to:
(1) an alkaline earth metal salt or an organic amine salt of a compound represented by the formula [I]:

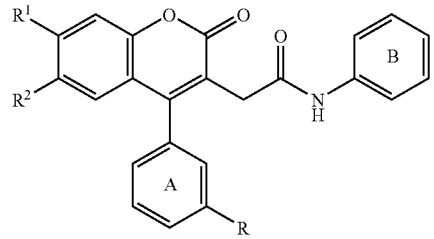

wherein $R^1$ and $R^2$ are each a hydrogen atom, a halogen atom, or an optionally substituted linear hydrocarbon group; ring A is an optionally further substituted benzene ring; B is an optionally substituted benzene ring; R is a carboxyl group or a linear hydrocarbon group substituted with a carboxyl group;

(2) the compound according to the above (1), which is an hydrate;

(3) the compound according to the above (1), wherein $R^1$ and $R^2$ are each a halogen atom or an optionally substituted $C_{1-7}$ alkyl group;

(4) the compound according to the above (1), wherein ring B is a benzene ring which is substituted with a halogenated alkyl group and/or a halogen atom;

(5) the compound according to the above (1), wherein R is a group represented by the formula —$(CH_2)_n$—R' wherein R' is an carboxyl group and n is an integer of 0 to 6;

(6) the compound according to the above (1), wherein R is a group represented by the formula —$(CH=CH)_{n''}$—R' wherein R' is a carboxyl group and n" is an integer of 1 to 3;

(7) the compound according to the above (1), which is an alkaline earth metal salt;

(8) the compound according to the above (7), wherein the alkaline earth metal salt is a calcium salt;

(9) the compound according to the above (1), which is an organic amine salt;

(10) the compound according to the above (9), wherein the organic amine salt is a primary amine salt;

(11) the compound according to the above (10), wherein the primary amine salt is a tris(hydroxymethyl)methylamine salt;

(12) a compound selected from the group consisting of mono-calcium bis((2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate), (2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate tris(hydroxymethyl)methylamine salt, (2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate diethanolamine salt, monocalcium bis(3-[3-[6-chloro-3-(2-[[4-fluoro-2-(trifluoromethyl)phenyl]amino]-2-oxoethyl)-7-methyl-2-oxo-2H-chromen-4-yl]phenyl]propionate) and monocalcium bis(4-[3-[7-chloro- 3-(2-[[4-fluoro-2-(trifluoromethyl)phenyl]amino]-2-oxoethyl)-6-methyl-2-oxo-2H-chromen-4-yl]phenyl] butanoate), or a hydrate thereof;

(13) a process for producing an alkaline earth metal salt of a compound represented by the formula [I]:

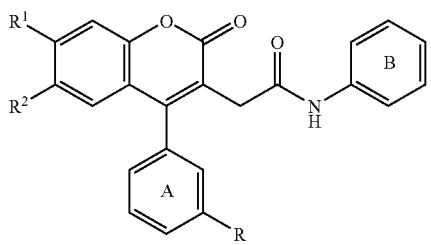

wherein each symbol is as defined above, which comprises reacting a compound represented by the formula [I] with an alkaline earth metal hydroxide or an alkaline earth metal hydride, or reacting an alkaline metal salt of a compound represented by the formula [I] with an alkaline earth metal halide;

(14) a crystal of the compound according to the above (1);
(15) a medicament comprising the compound according to the above (1) or a crystal thereof;
(16) the medicament according to the above (15), which is an oral preparation;
(17) the medicament according to the above (15), which is a lipid-rich plaque regressing agent or an ACAT inhibitor;
(18) the medicament according to the above (15), which is a prophylactic or therapeutic agent against coronary syndrome, myocardial infarction, unstable angina, coronary artery restenosis after PTCA or stent placement, peripheral artery occlusion, hyperlipemia, cerebral infarction, cerebral apoplexy, Alzheimer's disease, multiple risk syndrome or metabolic syndrome, or an agent for regressing, inhibiting progression of or stabilizing an arteriosclerotic or atherosclerotic lesion;
(19) the agent for regressing, inhibiting progression of or stabilizing an arteriosclerotic or atherosclerotic lesion according to the above (18), which is combined with a HMG-CoA reductase inhibitor;
(20) a method for regressing a lipid-rich plaque or inhibiting ACAT in a mammal, which comprises administering an effective amount of the compound according to the above (1) to the mammal;
(21) a method for preventing or treating coronary syndrome, myocardial infarction, unstable angina, coronary artery restenosis after PTCA or stent placement, peripheral artery occlusion, hyperlipemia, cerebral infarction, cerebral apoplexy, Alzheimer's disease, multiple risk syndrome or metabolic syndrome, or regressing, inhibiting progression of or stabilizing an arteriosclerotic or atherosclerotic lesion in a mammal, which comprises administering an effective amount of the compound according to the above (1) to the mammal;
(22) the method for regressing, inhibiting progression of or stabilizing an arteriosclerotic or atherosclerotic lesion according to the above (21), which comprises administering the compound according to the above (1) in combination with a HMG-CoA reductase inhibitor;
(23) use of the compound according to the above (1) for production of a lipid-rich plaque regressing agent or an ACAT inhibitor;
(24) use of the compound according to the above (1) for production of a prophylactic or therapeutic agent against coronary syndrome, myocardial infarction, unstable angina, coronary artery restenosis after PTCA or stent placement, peripheral artery occlusion, hyperlipemia, cerebral infarction, cerebral apoplexy, Alzheimer's disease, multiple risk syndrome or metabolic syndrome, or an agent for regressing, inhibiting progression of or stabilizing an arteriosclerotic or atherosclerotic lesion;
(25) the use of the compound according to the above (1) for production of an agent for regressing, inhibiting progression of or stabilizing an arteriosclerotic or atherosclerotic lesion according to the above (24), which is combined with a HMG-CoA reductase inhibitor; and the like.

DETAILED DESCRIPTION OF THE INVENTION

Figure 1:
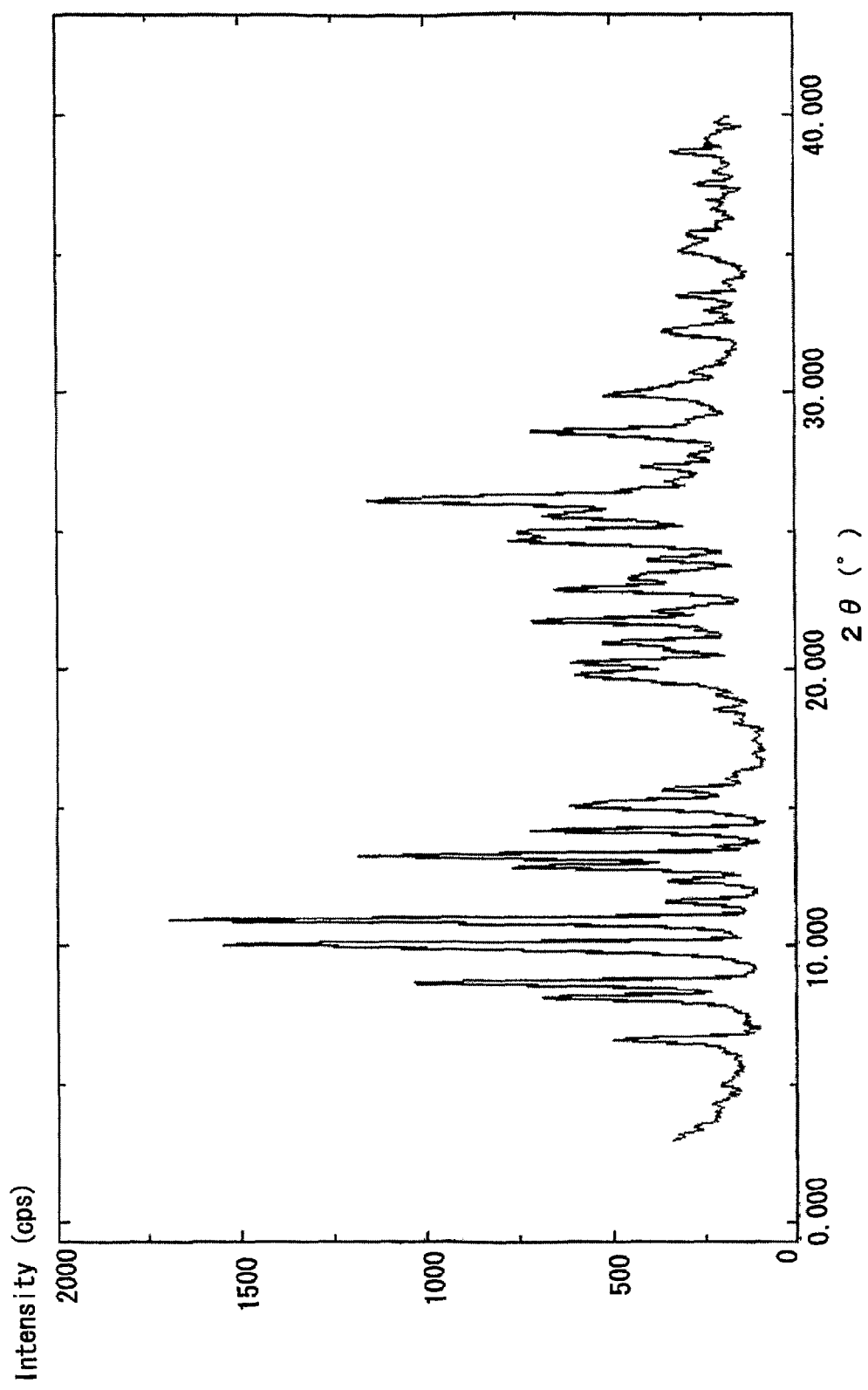
FIG. 1 is the X-ray powder diffraction pattern of the crystals obtained by Example 1.

In the formula [I], $R^1$ and $R^2$ are each a hydrogen atom, a halogen atom, or an optionally substituted linear hydrocarbon group.

As the "linear hydrocarbon group" of the "optionally substituted linear hydrocarbon group" represented by $R^1$ and $R^2$, for example, an alkyl group, an alkenyl group, an alkynyl group and the like are used. Alternatively, a group in which two or three of carbon-carbon bonds of an alkyl group are converted into double bonds, such as an alkadienyl group or an alkatrienyl group may be used.

As the alkyl group, for example, a linear or branched alkyl group having 1 to 7 carbon atoms is used and, preferably, for example, a linear or branched alkyl group having 1 to 4 carbon atoms such as methyl, ethyl, propyl, isopropyl, butyl, isobutyl, sec-butyl or tert-butyl is used.

As the alkenyl group, for example, an alkenyl group having 2 to 6 carbon atoms such as ethenyl, propenyl, isopropenyl, butenyl, isobutenyl or sec-butenyl is used and, preferably, for example, an alkenyl group having 2 to 4 carbon atoms such as ethenyl, propenyl, isopropenyl or isobutenyl is used.

As the alkynyl group, an alkynyl group having 2 to 6 carbon atoms such as ethynyl, propynyl, isopropynyl, butynyl, isobutynyl or sec-butynyl is used and, preferably, an alkynyl group having 2 to 4 carbon atoms such as ethynyl, propynyl, isopropynyl or isobutynyl is used.

Examples of the group in which two or three of carbon-carbon bonds of an alkyl group are converted into double bonds include a group in which two or three of carbon-carbon bonds of a linear or branched $C_{3-7}$ alkyl group (preferably, linear alkyl group) are converted into double bonds and, preferably, an alkadienyl group having 4 to 6 carbon atoms such as butadienyl, and an alkatrienyl group such as 1,3,5-hexatrienyl are used.

As the linear hydrocarbon group, a linear or branched alkyl group having 1 to 6 carbon atoms is preferable, and a linear or branched $C_{1-4}$ alkyl group such as methyl, ethyl, propyl, isopropyl, butyl, isobutyl, sec-butyl or tert-butyl is particularly preferable.

Examples of a substituent for the "optionally substituted linear hydrocarbon group" represented by $R^1$ and $R^2$ include an optionally substituted aryl group, an optionally substituted cycloalkyl group, an optionally substituted cycloalkenyl group, an optionally substituted heterocyclic group, an optionally substituted amino group, an optionally substituted hydroxyl group, an optionally substituted thiol group, an acyl group, a halogen atom (e.g. fluorine, chlorine, bromine, iodine), an oxo group, a carboxyl group, a nitro group, a cyano group, an optionally substituted alkyl group and the like. The "linear hydrocarbon group" may be substituted with 1 to 5 (preferably, 1 to 3) of these optional substituents at substitutable positions.

Examples of the "aryl group" of the "optionally substituted aryl group" include a $C_{6-16}$ aryl group such as phenyl, naphthyl, anthryl, phenanthryl, acenaphthylenyl and the like. Inter alia, a $C_{6-10}$ aryl group such as phenyl, 1-naphthyl, 2-naphthyl and the like is preferable. Examples of a substituent for the aryl group include (i) an optionally halogenated $C_{1-6}$ alkoxy group (e.g. methoxy, ethoxy, propoxy, trifluoromethoxy etc.), (ii) a halogen atom (e.g. fluorine, chlorine, bromine, iodine), (iii) an optionally halogenated $C_{1-6}$ alkyl group (e.g. methyl, ethyl, propyl, trifluoromethyl etc.) and the like. The aryl group may be substituted with 1 to 2 of these optional substituents.

Examples of the "cycloalkyl group" of the "optionally substituted cycloalkyl group" include a $C_{3-7}$ cycloalkyl group such as cyclopropyl, cyclobutyl, cyclopentyl, cyclohexyl, cycloheptyl and the like. A substituent for the cycloalkyl group and the number of the substituent are similar to those for the aforementioned optionally substituted aryl group.

Examples of the "cycloalkenyl group" of the "optionally substituted cycloalkenyl group" include a $C_{3-6}$ cycloalkenyl group such as cyclopropenyl, cyclobutenyl, cyclopentenyl, cyclohexenyl and the like. A substituent for the cycloalkenyl group and the number of the substituent are similar to those for the aforementioned optionally substituted aryl group.

Examples of the "heterocyclic group" of the "optionally substituted heterocyclic group" include an aromatic heterocyclic group and a saturated or unsaturated non-aromatic heterocyclic group (aliphatic heterocyclic group) which contain at least one, preferably 1 to 4 heteroatoms selected from oxygen, sulfur and nitrogen as an atom constituting a ring system (ring atom). Non-aromatic heterocyclic group is preferable.

Examples of the "aromatic heterocyclic group" include a 5 to 6-membered aromatic monocyclic heterocyclic group (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.) and an aromatic fused heterocyclic group in which 2 to 3 of 5- to 6-membered rings (the aforementioned 5 to 6-membered aromatic monocyclic heterocyclic ring, benzene ring etc.) are fused (e.g.: benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzoisothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thiantrenyl, phenathrizinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl etc.). Inter alia, a 5- to 6-membered aromatic monocyclic heterocyclic group such as furyl, thienyl, pyrazinyl, pyridyl and pyrimidinyl is preferable.

Examples of the "non-aromatic heterocyclic group" include a 4- to 9-membered non-aromatic monocyclic heterocyclic group such as oxiranyl, azetidinyl, oxetanyl, thietanyl, pyrrolidinyl, tetrahydrofuryl, thiolanyl, piperidinyl, tetrahydropyranyl, morpholinyl, thiomorpholinyl, piperazinyl and the like (in particular, 5- to 9-membered cyclic amino group which may contain 1 to 3 heteroatoms such as an oxygen atom or a sulfur atom in addition to a nitrogen atom, such as pyrrolidinyl, piperidinyl, piperazinyl, morpholinyl and 3,6-dihydropyridine-1(2H)-yl), a fused heterocyclic group of 1 to 2 (preferably 1) of the aforementioned non-aromatic monocyclic heterocyclic groups and 1 to 2 (preferably 1) of benzene rings, such as 2,3-dihydroindolyl, 1,3-dihydroisoindolyl and the like, a fused heterocyclic group of 1 to 2 (preferably 1) of the aforementioned non-aromatic monocyclic heterocyclic groups and 1 to 2 (preferably 1) of the aforementioned 5- to 6-membered aromatic monocyclic heterocyclic group, and a non-aromatic heterocyclic group in which a part or all of the double bonds of the aforementioned aromatic monocyclic heterocyclic group or aromatic fused heterocyclic group are saturated, such as 1,2,3,4-tetrahydroquinolyl, 1,2,3,4-tetrahydroisoquinolyl and the like.

The heterocyclic group may be substituted with 1 to 4, preferably 1 to 2 substituents. Examples of such a substituent include an optionally halogenated $C_{1-6}$ alkyl group (e.g. methyl, ethyl, propyl, n-butyl, n-hexyl etc.), an optionally halogenated $C_{6-12}$ aryl group (e.g. phenyl), a hydroxy-$C_{6-12}$ aryl group (e.g. 4-hydroxyphenyl), an optionally halogenated $C_{1-4}$ alkylsulfonyl group (e.g. methylsulfonyl), a $C_{7-15}$ aralkyl group (e.g. benzyl), an optionally halogenated $C_{1-4}$ alkoxy-$C_{1-4}$ alkyl group (e.g. propoxyethyl etc.), a 5- to 9-membered heterocyclic group which contains 1 to 3 heteroatoms such as a nitrogen atom, an oxygen atom and a sulfur atom in addition to carbon atoms (e.g. piperidyl, piperazinyl, morpholinyl, thienyl, furyl, pyridinyl, pyrimidinyl, thiazolyl, benzothiazolyl, benzoisothiazolyl, benzoxazolyl, benzisoxazolyl etc.), a hydroxy group, an oxo group, a thioxo group and the like.

Examples of a substituent for the "optionally substituted amino group" (including an amino group and a mono- or di-substituted amino group) include an optionally halogenated lower ($C_{1-6}$) alkyl group (e.g. methyl, ethyl, propyl etc.), an optionally halogenated $C_{6-12}$ aryl group (e.g. phenyl), a 5- to 9-membered heterocyclic group which contains 1 to 3 heteroatoms such as a nitrogen atom, an oxygen atom and a sulfur atom in addition to carbon atoms (e.g. thienyl, furyl, pyridyl, pyrimidinyl, thiazolyl, benzothiazolyl, benzisothiazolyl, benzoxazolyl, benzisoxazolyl etc.), an optionally halogenated $C_{1-4}$ alkyl-carbonyl group (e.g. methylcarbonyl, ethylcarbonyl etc.), a $C_{6-12}$ aryl-carbonyl group (e.g. benzoyl etc.), an optionally halogenated $C_{1-4}$ alkyl-sulfonyl group, and an optionally halogenated $C_{1-4}$ alkoxy-$C_{1-4}$ alkyl group. In addition, the two substituents of a di-substituted amino group may be taken together with the nitrogen atom to form a "cyclic amino group". The "cyclic amino group" includes a 3- to 8-membered (preferably 5- to 6-membered) cyclic amino group such as 1-azetidinyl, 1-pyrrolidinyl, piperidinyl, morpholinyl, thiomorpholinyl (the sulfur atom may be oxidized), and 1-piperazinyl which may be substituted at the 4-position with optionally halogenated lower alkyl (e.g. $C_{1-6}$ alkyl such as methyl, ethyl, propyl, isopropyl, butyl, tert-butyl, pentyl, hexyl etc.), optionally halogenated aralkyl (e.g. $C_{7-10}$ aralkyl such as benzyl, phenethyl etc.), optionally halogenated aryl (e.g. $C_{6-10}$ aryl such as phenyl, 1-naphthyl, 2-naphthyl etc.) or the like.

Examples of the "optionally substituted alkyl group" include a $C_{1-6}$ alkyl group (e.g. methyl, ethyl, propyl, n-butyl, n-hexyl etc.) which may be substituted with a halogen atom (e.g. fluorine, chlorine, bromine, iodine) or the like.

Examples of the "optionally substituted hydroxyl group" include a hydroxyl group, an optionally halogenated $C_{1-16}$ alkoxy group, preferably an optionally halogenated $C_{1-4}$ alkoxy group, more preferably a $C_{1-4}$ alkoxy group (e.g. methoxy, ethoxy, propoxy, butoxy, t-butoxy etc.), a $C_{1-6}$ alkyl-carbonyloxy group (e.g. methylcarbonyloxy, ethylcarbonyloxy, butylcarbonyloxy etc.), an aminocarbonyloxy group, and a mono- or di-$C_{1-4}$ alkylaminocarbonyloxy group.

Examples of the "optionally substituted thiol group" include a thiol group, an optionally halogenated $C_{1-16}$ alkylthio group, preferably optionally halogenated $C_{1-4}$ alkylthio group, more preferably $C_{1-4}$ alkylthio group (e.g. methylthio, ethylthio etc.) and a 5- to 9-membered heterocycle, containing 1 to 3 heteroatoms such as a nitrogen atom, an oxygen atom and a sulfur atom in addition to carbon atoms (e.g. thienyl, furyl, pyridyl, pyrimidinyl, thiazolyl, benzothiazolyl, benzisothiazolyl, benzoxazolyl, benzisoxazolyl etc.), -thio group (e.g. 2-pyridylthio).

Examples of the "acyl group" include a formyl group, a $C_{1-6}$ alkyl-carbonyl group (preferably $C_{1-4}$ alkyl-carbonyl group (e.g. methylcarbonyl, ethylcarbonyl)), a $C_{1-4}$ alkoxycarbonyl group (e.g. methoxycarbonyl), an optionally halogenated $C_{1-6}$ alkyl-sulfonyl group (preferably $C_{1-4}$ alkyl-sulfonyl group (e.g. methylsulfonyl, ethylsulfonyl)), an optionally halogenated $C_{1-6}$ alkyl-sulfinyl group (preferably $C_{1-4}$ alkyl-sulfinyl group (e.g. methylsulfinyl, ethylsulfinyl)), a $C_{1-4}$ alkoxy-sulfonyl group (e.g. methoxysulfonyl), a benzyloxycarbonyl group, a $C_{3-6}$ cycloalkyl-carbonyl group, a carbamoyl group, a mono- or di-$C_{1-4}$ alkylcarbamoyl group and the like.

More specifically, as a substituent for the linear hydrocarbon group, 1 to 4 substituents selected from a halogen atom; an amino group; a mono- or di-$C_{1-4}$ alkylamino group; a carboxyl group; a $C_{1-4}$ alkoxycarbonyl group; a hydroxy group; an optionally halogenated $C_{1-4}$ alkoxy group; a $C_{3-6}$ cycloalkyl group; a nitro group; a cyano group; an optionally halogenated $C_{1-4}$ alkylthio group; a cyclic amino group substituted with 1 to 2 substituents selected from (i) a $C_{1-4}$ alkyl group, (ii) a $C_{1-4}$ alkylsulfonyl group, (iii) a $C_{6-12}$ aryl group which may be substituted with a halogen atom or a hydroxy group, (iv) a $C_{7-15}$ aralkyl group, (v) a $C_{1-4}$ alkoxy-$C_{1-4}$ alkyl group, (vi) a 5- to 9-membered heterocyclic group containing 1 to 3 heteroatoms such as a nitrogen atom, an oxygen atom and a sulfur atom in addition to carbon atoms and (vii) a hydroxy group (e.g. 5- to 9-membered cyclic amino group which may contain 1 to 3 heteroatoms such as oxygen atom and sulfur atom in addition to a nitrogen atom, more specifically, for example, pyrrolidinyl, piperidinyl, piperazinyl, morpholinyl etc.); a $C_{1-4}$ alkyl-carbonylamino group; an aminocarbonyloxy group; a mono- or di-$C_{1-4}$ alkylaminocarbonyloxy group; a $C_{1-4}$ alkylsulfonylamino group; a $C_{1-4}$ alkoxy-carbonyl group; a benzyloxycarbonyl group; a carboxyl group; a $C_{1-6}$ alkyl-carbonyl group; a $C_{3-6}$ cycloalkyl-carbonyl group; a carbamoyl group; a mono- or di-$C_{1-4}$ alkylcarbamoyl group; a $C_{1-6}$ alkylsulfonyl group; a $C_{1-6}$ alkyl-carbonyloxy group; an amino group substituted with $C_{1-4}$ alkyl and a 5- to 9-membered heterocyclic group containing 1 to 3 heteroatoms such as a nitrogen atom, an oxygen atom and a sulfur atom in addition to carbon atoms; an amino group substituted with $C_{1-4}$ alkyl and $C_{1-4}$ alkyl-carbonyl; an amino group substituted with $C_{1-4}$ alkyl and $C_{6-12}$ aryl-carbonyl; a $C_{1-6}$ alkyl-carbonyloxy group; a mono or di-$C_{1-4}$ alkoxy-$C_{1-4}$ alkyl-amino group; a 5- to 9-membered heterocycle, containing 1 to 3 heteroatoms such as a nitrogen atom, an oxygen atom and a sulfur atom in addition to carbon atoms, -thio group; and an oxo group are used.

As each of $R^1$ and $R^2$, a halogen atom (e.g. a fluorine atom, a chlorine atom, a bromine atom), an optionally substituted $C_{1-7}$ alkyl group (preferably $C_{1-4}$ alkyl group such as methyl, ethyl and propyl, particularly preferably methyl), an optionally substituted $C_{2-6}$ alkenyl group (preferably ethenyl) and the like are preferable. Inter alia, a halogen atom and an optionally substituted $C_{1-7}$ alkyl group are preferable. The "$C_{1-7}$ alkyl group" of the "optionally substituted $C_{1-7}$ alkyl group" may have an oxo group as such a substituent. When the $C_{1-7}$ alkyl group is substituted with an oxo group at the α-position, it may form a $C_{1-7}$ alkanoyl group such as formyl and acetyl.

As a substituent for the "optionally substituted $C_{1-7}$ alkyl group", preferred are, for example, (i) a hydroxy group,
(ii) a mono- or di-$C_{1-4}$ alkylamino group (e.g. dimethylamino, diethylamino),
(iii) an amino group substituted with $C_{1-4}$ alkyl and a 5- to 9-membered heterocyclic group containing 1 to 3 heteroatoms such as a nitrogen atom, an oxygen atom and a sulfur atom in addition to carbon atoms (e.g. thienyl, furyl, pyridyl, pyrimidinyl, thiazolyl, benzothiazoyl, benzisothiazolyl, benzoxazolyl, benzisoxazolyl etc.) (e.g. methyl(2-pyridyl)amino),
(iv) an amino group substituted with $C_{1-4}$ alkyl and $C_{1-4}$ alkyl-carbonyl (e.g. methyl(methylcarbonyl)amino),
(v) an amino group substituted with $C_{1-4}$ alkyl and $C_{6-12}$ aryl-carbonyl (e.g. methyl(benzoyl)amino),
(vi) a mono or di-$C_{1-4}$ alkoxy-$C_{1-4}$ alkyl-amino group (e.g. butoxypropylamino),
(vii) a 5- to 9-membered cyclic amino group which may contain 1 to 3 heteroatoms such as an oxygen atom and a sulfur atom in addition to a nitrogen atom, which may be substituted with $C_{6-12}$ aryl optionally substituted with 1 to 4 substituents selected from $C_{1-4}$ alkyl (e.g. methyl), a halogen atom, a hydroxy group and optionally halogenated $C_{1-4}$ alkyl (e.g. phenyl, 4-hydroxyphenyl, 4-chlorophenyl, 3-methylphenyl), $C_{1-4}$ alkylsulfonyl (e.g. methylsulfonyl), $C_{7-15}$ aralkyl optionally substituted with 1 to 4 substituents selected from a halogen atom, hydroxy group and optionally halogenated $C_{1-4}$ alkyl (e.g. benzyl), $C_{1-4}$ alkoxy-$C_{1-4}$ alkyl (e.g. propoxyethyl etc.), a 5- to 9-membered heterocyclic group containing 1 to 3 heteroatoms such as a nitrogen atom, an oxygen atom and a sulfur atom in addition to carbon atoms (e.g. piperidyl, piperazinyl, morpholinyl, thienyl, furyl, pyridyl, pyrimidinyl, thiazolyl, benzothiazolyl, benzisothiazolyl, benzoxazolyl, benzisoxazolyl), a hydroxy group and the like (e.g. pyrrolidinyl, piperidyl, piperazinyl, morpholinyl, 3,6-dihydropyridin-1(2H)-yl) (preferably piperazinyl substituted with a phenyl group at the 4-position; wherein the phenyl group may be halogenated),
(viii) a $C_{1-6}$ alkyl-carbonyloxy group (e.g. methylcarbonyloxy, ethylcarbonyloxy, butylcarbonyloxy etc.),
(ix) a 5- to 9-membered heterocycle, containing 1 to 3 heteroatoms such as a nitrogen atom, an oxygen atom and a sulfur atom in addition to carbon atoms (e.g. thienyl, furyl, pyridyl, pyrimidinyl, thiazolyl, benzothiazolyl, benzisothiazolyl, benzoxazolyl, benzisoxazolyl etc.), -thio group (e.g. 2-pyridylthio).

As a substituent for the $C_{2-6}$ alkenyl group, for example, $C_{1-4}$ alkoxy-carbonyl (e.g. methoxycarbonyl) is preferable.

As $R^1$ and $R^2$, a halogen atom, an optionally substituted $C_{1-7}$ alkyl group and the like (in particular, methyl) are preferable, respectively, and particularly, $R^1$ is a halogen atom and $R^2$ is a $C_{1-7}$ alkyl group (in particular, methyl).

In the formula [I], ring A represents an optionally further substituted benzene ring.

In the formula [I], ring B represents an optionally substituted benzene ring.

In the formula [I], a substituent for an optionally further substituted benzene ring represented by ring A or an optionally substituted benzene ring represented by ring B includes (i) an optionally halogenated $C_{1-4}$ alkyl group (e.g. methyl, chloromethyl, difluoromethyl, trichloromethyl, trifluoromethyl, ethyl, 2-bromoethyl, 2,2,2-trifluoroethyl, propyl, isopropyl, 3,3,3-trifluoropropyl, butyl etc.);

(ii) a $C_{1-4}$ alkyl group substituted with an amino group (e.g. aminomethyl, 2-aminoethyl etc.);

(iii) a $C_{1-4}$ alkyl group substituted with a mono- or di-$C_{1-4}$ alkylamino group (e.g. methylaminomethyl, dimethylaminomethyl, 2-methylaminoethyl, 2-dimethylaminoethyl etc.);

(iv) a $C_{1-4}$ alkyl group substituted with a carboxyl group (e.g. carboxymethyl, carboxyethyl etc.);

(v) a $C_{1-4}$ alkyl group substituted with a $C_{1-4}$ alkoxy-carbonyl group (e.g. methoxycarbonylethyl, ethoxycarbonylethyl, etc.);

(vi) a $C_{1-4}$ alkyl group substituted with a hydroxy group (e.g. hydroxymethyl, hydroxyethyl etc.);

(vii) a $C_{1-4}$ alkyl group substituted with a $C_{1-4}$ alkoxy group which may be substituted with a $C_{1-4}$ alkoxy group or a phenoxy group (e.g. methoxymethyl, methoxyethyl, ethoxyethyl etc.);

(viii) a $C_{3-6}$ cycloalkyl group (e.g. cyclopropyl, cyclobutyl, cyclopentyl, cyclohexyl etc.);

(ix) a halogen atom (e.g. fluorine, chlorine, bromine, iodine);

(x) a nitro group;

(xi) a cyano group;

(xii) a hydroxy group;

(xiii) an optionally halogenated $C_{1-4}$ alkoxy group (e.g. methoxy, difluoromethoxy, trifluoromethoxy, ethoxy, 2,2,2-trifluoroethoxy, propoxy, butoxy, isopropoxy etc.), $C_{1-4}$ alkoxy group which may be substituted with a $C_{1-4}$ alkoxy group or a phenoxy group;

(xiv) an optionally halogenated $C_{1-4}$ alkylthio group (e.g. methylthio, difluoromethylthio, trifluoromethylthio, ethylthio, propylthio, isopropylthio, butylthio etc.), a $C_{1-4}$ alkylthio group which may be substituted with a $C_{1-4}$ alkoxy group or a phenoxy group;

(xv) an amino group;

(xvi) a mono- or di-$C_{1-4}$ alkylamino group (e.g. methylamino, ethylamino, propylamino, dimethylamino, diethylamino, etc.);

(xvii) a cyclic amino group (e.g. 5- to 9-membered cyclic amino group which may contain 1 to 3 heteroatoms such as an oxygen atom and a sulfur atom in addition to the nitrogen atom, specifically, pyrrolidinyl, piperidyl, piperazinyl, morpholinyl etc.);

(xviii) a $C_{1-4}$ alkyl-carbonylamino group (e.g. acetylamino, propionylamino, butyrylamino etc.);

(xix) an aminocarbonyloxy group;

(xx) a mono- or di-$C_{1-4}$ alkylamino-carbonyloxy group (e.g. methylaminocarbonyloxy, ethylaminocarbonyloxy, dimethylaminocarbonyloxy, diethylaminocarbonyloxy etc.);

(xxi) a $C_{1-4}$ alkylsulfonylamino group (e.g. methylsulfonylamino, ethylsulfonylamino, propylsulfonylamino etc.);

(xxii) a $C_{1-4}$ alkoxy-carbonyl group (e.g. methoxycarbonyl, ethoxycarbonyl, propoxycarbonyl, isobutoxycarbonyl etc.);

(xxiii) a benzyloxycarbonyl group;

(xxiv) a carboxyl group;

(xxxv) a $C_{1-6}$ alkyl-carbonyl group (e.g. methylcarbonyl, ethylcarbonyl, butylcarbonyl etc.);

(xxvi) a $C_{3-6}$ cycloalkyl-carbonyl (e.g. cyclohexylcarbonyl etc.);

(xxvii) a carbamoyl group;

(xxviii) a mono- or di-$C_{1-4}$ alkylcarbamoyl group (e.g. methylcarbamoyl, ethylcarbamoyl, propylcarbamoyl, butylcarbamoyl, diethylcarbamoyl, dibutylcarbamoyl etc.);

(xxix) a $C_{1-6}$ alkylsulfonyl group (e.g. methylsulfonyl, ethylsulfonyl, propylsulfonyl etc.); $C_{3-6}$ cycloalkylsulfonyl (e.g. cyclopentylsulfonyl, cyclohexylsulfonyl etc.);

(xxx) a $C_{1-6}$ alkyl group substituted with a cyclic amino group (e.g. 5- to 9-membered cyclic amino group which may contain 1 to 3 heteroatoms such as an oxygen atom and a sulfur atom in addition to the nitrogen atom, specifically, pyrrolidinyl, piperidyl, piperazinyl, 3,6-dihydropyridin-1(2H)-yl, [1,3]thiazolo[4,5-b]pyridin-3 (2H)-yl, morpholinyl etc.) substituted with 1 or 2 substituents selected from (a) $C_{1-4}$ alkyl (e.g. methyl), (b) $C_{1-4}$ alkylsulfonyl (e.g. methylsulfonyl), (c) a $C_{6-12}$ aryl group which may have optionally halogenated $C_{1-4}$ alkyl (e.g. methyl, trifluoromethyl), halogen (e.g. fluorine, chlorine) or a hydroxy group (e.g. phenyl, naphthyl, hydroxyphenyl, methylphenyl, chlorophenyl etc.), (d) $C_{7-15}$ aralkyl (e.g. benzyl etc.), (e) $C_{1-4}$ alkoxy-$C_{1-4}$ alkyl (e.g. propoxyethyl etc.), (f) a 5- to 9-membered heterocyclic group containing 1 to 3 heteroatoms such as a nitrogen atom, an oxygen atom and a sulfur atom in addition to carbon atoms (e.g. piperidyl, piperazinyl, morpholinyl, thienyl, furyl, pyridyl, pyrimidinyl, thiazolyl, benzothiazolyl, benzisothiazolyl, benzoxazolyl, benzisoxazolyl etc.), (g) hydroxy, thiol, oxo and thioxo (e.g. morpholinomethyl, 4-phenyl-1-piperazinylmethyl, 2-morpholinoethyl, 3-piperazinylpropyl, 4-methylsulfonyl-piperazinylmethyl, 4-benzyl-1-piperazinylmethyl, 4-(4-hydroxyphenyl)-1-piperazinylmethyl, 4-hydroxypiperidinylmethyl, 4-hydroxy-4-phenyl-piperidylmethyl, 4-phenylpiperidylmethyl, 4-(2-pydyl)-1-piperazinylmethyl, 4-(4-hydroxyphenyl)-1-piperazinylmethyl, (4-phenyl-3,6-dihydropyridin-1 (2H)-yl)methyl etc.);

(xxxi) a $C_{1-4}$ alkyl group substituted with a $C_{1-6}$ alkyl-carbonyloxy group (e.g. methylcarbonyloxy, ethylcarbonyloxy, butylcarbonyloxy, etc.);

(xxxii) a $C_{1-4}$ alkyl group substituted with an amino group substituted with $C_{1-4}$ alkyl and a 5- to 9-membered heterocyclic group containing 1 to 3 heteroatoms such as a nitrogen atom, an oxygen atom and a sulfur atom in addition to carbon atoms (e.g. thienyl, furyl, pyridyl, pyrimidinyl, thiazolyl, benzothiazolyl, benzisothiazolyl, benzoxazolyl, benzisoxazolyl etc.) (e.g. methyl(2-pyridyl)amino);

(xxxiii) a $C_{1-4}$ alkyl group substituted with an amino group substituted with $C_{1-4}$ alkyl and $C_{1-4}$ alkyl-carbonyl (e.g. methyl(methylcarbonyl)amino);

(xxxiv) a $C_{1-4}$ alkyl group substituted with an amino group substituted with $C_{1-4}$ alkyl and $C_{6-12}$ aryl-carbonyl (e.g. methyl(benzoyl)amino);

(xxxv) a $C_{1-4}$ alkyl group substituted with a $C_{1-6}$ alkyl-carbonyloxy group (e.g. methylcarbonyloxy, ethylcarbonyloxy, butylcarbonyloxy etc.);

(xxxvi) a $C_{1-4}$ alkyl group substituted with a mono or di-$C_{1-4}$ alkoxy-$C_{1-4}$ alkyl-amino group (e.g. butoxypropylamino);

(xxxvii) a $C_{1-4}$ alkyl group substituted with a 5- to 9-membered heterocycle, containing 1 to 3 heteroatoms such as a nitrogen atom, an oxygen atom and a sulfur atom in addition to carbon atoms (e.g. thienyl, furyl, pyridyl, pyrimidinyl, thiazolyl, benzothiazolyl, benzisothiazolyl, benzoxazolyl, benzisoxazolyl, etc.), -thio group (e.g. 2-pyridylthio);

(xxxviii) an oxo group;

(xxxiv) a $C_{1-4}$ alkoxy-carbonyl $C_{2-6}$ alkenyl group (e.g. methoxycarbonylvinyl etc.);

(xxxx) a $C_{2-6}$ alkenyl group substituted with a carboxyl group (e.g. carboxyvinyl etc.);

(xxxxi) a $C_{1-4}$ alkyl group substituted with a cyano group (e.g. cyanomethyl etc.);

(xxxxii) a $C_{6-10}$ aryl group (e.g. phenyl, naphthyl etc.), phenoxy, benzoyl, phenoxycarbonyl, phenyl-$C_{1-4}$ alkylcarbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino [each phenyl group or each naphthyl group may be substituted with 1 to 3 substituents such as a $C_{1-4}$ alkyl group (e.g. methyl, ethyl, propyl, butyl, isopropyl etc.), a $C_{1-4}$ alkoxy group (e.g. methoxy, ethoxy, n-propyloxy, i-propyloxy, n-butyloxy etc.), a halogen atom (e.g. chloro, bromo, iodo etc.), a hydroxy group, a benzyloxy group, an amino group, a mono- or di-$C_{1-4}$ alkylamino group (e.g. methylamino, dimethylamino, ethylamino, diethylamino, diisopropylamino etc.), a nitro group, and a $C_{1-6}$ alkylcarbonyl group (e.g. 1-oxoethyl, 1-oxopropyl, 1-oxobutyl etc.) at substitutable position] and the like. The benzene ring or the aromatic ring may be substituted with 1 to 5, preferably 1 to 3 of these substituents at substitutable positions, wherein these substituents may be the same as or different from each other.

Preferable examples of such a substituent include (i) a halogen atom (e.g. fluorine, chlorine, bromine etc.), (ii) an optionally halogenated $C_{1-4}$ alkyl group (e.g. methyl, chloromethyl, difluoromethyl, trifluoromethyl, ethyl, propyl, isopropyl etc.), (iii) a $C_{3-6}$ cycloalkyl group (e.g. cyclopropyl, cyclobutyl etc.), (iv) a hydroxy group, (v) an optionally halogenated $C_{1-4}$ alkoxy group (e.g. methoxy, difluoromethoxy, trifluoromethoxy, ethoxy etc.), (vi) an optionally halogenated $C_{1-4}$ alkylthio group (e.g. methylthio, trifluoromethylthio, ethylthio, etc.), (vii) an amino group, (viii) a mono- or di-$C_{1-4}$ alkylamino group (e.g. methylamino, ethylamino, dimethylamino, diethylamino etc.), (ix) a $C_{1-4}$ alkoxy-carbonyl group (e.g. methoxycarbonyl, ethoxycarbonyl etc.), (x) a $C_{1-6}$ alkyl group substituted with a cyclic amino group (e.g. 5- to 9-membered cyclic amino group which may contain 1 to 3 heteroatoms such as an oxygen atom and a sulfur atom in addition to the nitrogen atom, specifically, pyrrolidinyl, piperidyl, morpholinyl etc.) which may be substituted with $C_{6-12}$ aryl group (e.g. phenyl, naphthyl etc.) (e.g. morpholinomethyl, 4-phenyl-1-piperazinylmethyl, 2-morpholinoethyl, 3-piperazinylpropyl etc.) and (xi) a carboxyl group. Particularly preferred are (i) a halogen atom (e.g. fluoro, chloro etc.), (ii) $C_{1-4}$ alkyl (e.g. methyl, ethyl etc.) (iii) a $C_{3-6}$ cycloalkyl group (e.g. cyclopropyl, cyclobutyl, etc.), (iv) a hydroxy group, (v) a $C_{1-4}$ alkoxy group (e.g. methoxy, ethoxy etc.), (vi) a $C_{1-6}$ alkyl group substituted with a cyclic amino group (e.g. 5- to 9-membered cyclic amino group which may contain 1 to 3 heteroatoms such as an oxygen atom and a sulfur atom in addition to the nitrogen atom, specifically, pyrrolidinyl, piperidyl, piperazinyl, 3,6-dihydropyridin-1(2H)-yl, morpholinyl, etc.) which may be substituted with a $C_{6-12}$ aryl group (e.g. phenyl, naphthyl etc.) (e.g. morpholinomethyl, 4-phenyl-1-piperazinylmethyl, 2-morpholinoethyl, (4-phenyl-3,6-dihydropyridin-1(2H)-ylmethyl), 3-piperazinylpropyl etc.) and (vii) a carboxyl group.

As ring A, a benzene ring which may be further substituted with an alkyl group, a halogenated alkyl group or a halogen atom in addition to the substituent represented by R is preferable, a benzene ring which may be further substituted with a $C_{1-6}$ alkyl group, a halogenated $C_{1-4}$ alkyl group or a halogen atom in addition to the substituent represented by R is further preferable, and a benzene ring substituted with only the substituent represented by R is particularly preferable.

As ring B, a benzene ring which may be substituted with a halogenated alkyl group and/or a halogen atom is preferable and, inter alia, a benzene ring which may be substituted with a halogenated $C_{1-4}$ alkyl group (preferably trifluoromethyl) and/or a halogen atom is particularly preferable (more preferably, a benzene ring substituted with a halogenated $C_{1-4}$ alkyl group and/or a halogen atom).

In the formula [I], R represents a carboxyl group or a linear hydrocarbon group substituted with a carboxyl group.

As the "linear hydrocarbon group" of the "linear hydrocarbon group substituted with a carboxyl group" represented by R, for example, an alkyl group, an alkenyl group, an alkynyl group and the like are used. Alternatively, a group in which two or three of carbon-carbon bonds of an alkyl group are converted into double bonds, such as an alkadienyl group may be used.

As the alkyl group, for example, a linear or branched alkyl group having 1 to 7 carbon atoms is used and, preferably, for example, a linear or branched alkyl group having 1 to 4 carbon atoms such as methyl, ethyl, propyl, isopropyl, butyl, isobutyl, sec-butyl or tert-butyl is used.

As the alkenyl group, for example, an alkenyl group having 2 to 6 carbon atoms such as ethenyl, propenyl, isopropenyl, butenyl, isobutenyl or sec-butenyl is used and, preferably, for example, an alkenyl group having 2 to 4 carbon atoms such as ethenyl, propenyl or isopropenyl is used.

As the alkynyl group, an alkynyl group having 2 to 6 carbon atoms such as ethynyl, propynyl, isopropynyl, butynyl, isobutynyl or sec-butynyl is used and, preferably, an alkynyl group having 2 to 4 carbon atoms such as ethynyl, propynyl or isopropynyl is used.

Examples of the group in which two or three of carbon-carbon bonds of an alkyl group are converted into double bonds include a group in which two or three of carbon-carbon bonds of a linear or branched $C_{3-7}$ alkyl group (preferably, linear alkyl group) are converted into double bonds and, preferably, an alkadienyl group having 4 to 6 carbon atoms such as butadienyl, and a 1,3,5-hexatrienyl are used.

As the linear hydrocarbon group, a linear or branched alkyl group having 1 to 6 carbon atoms is preferable, and a linear or branched $C_{1-4}$ alkyl group such as methyl, ethyl, propyl, isopropyl, butyl, isobutyl, sec-butyl or tert-butyl is particularly preferable.

As R, a group represented by the formula —$(CH_2)_n$—R', wherein R' represents a carboxyl group and n represents an integer of 0 to 6; a group represented by the formula —CH=CH—$(CH_2)_{n'}$—R', wherein R' represents a carboxyl group and n' represents an integer of 0 to 4; and a group represented by the formula —$(CH=CH)_{n''}$—R', wherein R' represents a carboxyl group and n" represents an integer of 1 to 3, are preferable. Inter alia, a group represented by the formula —$(CH_2)_n$—R' and a group represented by the formula $(CH=CH)_{n''}$—R' are preferable. n is preferably an integer of 1 to 4 (more preferably 2 or 3), n' is preferably an integer of 0 to 2 (more preferably 0), and n" is preferably an integer of 1 to 2 (more preferably 1).

The alkaline earth metal salt or the organic amine salt of the compound represented by the formula [I] (hereinafter, abbreviated as the compound of the present invention in some cases) may be any alkaline earth metal salts or organic amine salts, if those are pharmaceutically acceptable alkaline earth metal salts or organic amine salts. Examples of such an alkaline earth metal salt include salts of the carboxyl group which the compound represented by the formula [I] has with an alkaline earth metal such as calcium, magnesium etc. Examples of such an organic amine salt include salts of the carboxyl group which the compound represented by the formula [I] has with an organic bases (e.g. primary amines such as tris(hydroxymethyl)methylamine, ethanolamine and the like; organic amines such as trimethylamine, triethylamine, pyridine, picoline, diethanolamine, triethanolamine, dicyclohexylamine, N,N'-dibenzylethylenediamine and the like; and basic amino acids such as arginine, lysine, ornithine and the like).

As the alkaline earth metal salt of the compound represented by the formula [I], the calcium salt is preferable.

As the organic amine salt of the compound represented by the formula [I], the primary amine salt is preferable, and the tris(hydroxymethyl)methylamine is particularly preferable.

As the compound of the present invention, the alkaline earth metal salt of the compound represented by the formula [I] is preferable, and the calcium salt of the compound represented by the formula [I] is particularly preferable.

The compound of the present invention may be a crystal, and both a single crystal form and a mixture of polymorphic crystal forms are encompassed in the scope of the compound of the present invention. Crystals can be produced by crystallization according to a crystallization method known per se. The compound of the present invention is preferably a crystal. As the crystal of the compound of the present invention, the crystal of the alkaline earth metal salt (in particular, the calcium salt) of the compound represented by the formula [I] is easy to obtain, and is easy to isolate and purify. Accordingly, the alkaline earth metal salt (in particular, the calcium salt) of the compound represented by the formula [I] is particularly preferable as an active ingredient of a medicament.

In addition, the compound of the present invention may be a solvate (e.g. hydrate etc.), and both solvate and non-solvate (e.g. non-hydrate etc.) are encompassed in the scope of the present invention. The hydration number of the compound of the present invention may vary with the humidity continuously, and a range of the hydration number may be from non-hydrate to decahydrate, preferably from monohydrate to tetrahydrate.

In addition, the compound of the present invention may be labelled with an isotope element (e.g. $^3H$, $^{14}C$, $^{35}S$, $^{125}I$ etc.).

Among the compound of the present invention, monocalcium bis((2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate); (2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate tris (hydroxymethyl)methylamine salt; (2E)-3-[3-[7-chloro-3-(2-[[4-fluoro-2-(trifluoromethyl)phenyl]amino]-2-oxoethyl)-6-methyl-2-oxo-2H-chromen-4-yl]phenyl] acrylate diethanolamine salt; monocalcium bis(3-[3-[6-chloro-3-(2-[[4-fluoro-2-(trifluoromethyl)phenyl]amino]-2-oxoethyl)-7-methyl-2-oxo-2H-chromen-4-yl]phenyl] propionate); monocalcium bis(4-[3-[7-chloro-3-(2-[[4-fluoro-2-(trifluoromethyl)phenyl]amino]-2-oxoethyl)-6-methyl-2-oxo-2H-chromen-4-yl]phenyl]butanoate); a hydrate thereof and the like are used preferably.

The alkaline earth metal salt of the compound represented by the formula [I] can be produced by reacting the compound represented by the formula [I] with an alkaline earth metal hydroxide or an alkaline earth metal hydride, or reacting an alkaline metal salt of the compound represented by the formula [I] with an alkaline earth metal halide.

Alternatively, the alkaline earth metal salt of the compound represented by the formula [I] can be produced by reacting the ammonium salt of the compound represented by the formula [I] with an alkaline earth metal halide.

The compound of the present invention can also be produced from the compound represented by the formula [I] by a method known per se or the similar method. It is also possible to exchange salts by a method known per se or the similar method.

The compound represented by the formula [I] can be prepared according to the method disclosed, for example, in EP-A 585913, EP-A 602598, JP-A 6-263736, WO 02/06264 or WO 03/059900.

When there exist optical isomers of the compound of the present invention, these individual optical isomers and a mixture thereof are included in the scope of the present invention. If desired, these isomers may be optically resolved according to a known per se means, or may be prepared individually.

Since the compound of the present invention is low toxic and safe (for example, more superior as a medicament from the aspects of acute toxicity, chronic toxicity, genetic toxicity, reproductive toxicity, cardiac toxicity, drug interaction, cardinogenicity and the like) and has lipid-rich plaque regressing activity, the compound of the present invention is useful for preventing or treating (acute) coronary syndrome such as myocardial infarction, unstable angina and the like; peripheral artery occlusion, restenosis after percutaneous coronary plasty (PTCA), restenosis after stent placement, ischemic heart failure such as myocardial infarction and angina, arteriosclerosis, intermittent claudication, cerebral apoplexy (e.g. cerebral infarction, cerebral embolus, cerebral hemorrhage), lacunar infarction, cerebral vascular dementia, xanthomatosis and the like of a mammal (e.g. mouse, rat, rabbit, dog, cat, cow, pig, monkey, human, etc.), and are useful as a defoaming agent.

Further, the compound of the present invention has ACAT inhibitory activity (preferably, macrophage ACAT inhibitory activity, subtype 1 ACAT inhibitory activity), and can be used as a safe prophylactic or therapeutic agent against hypercholesterolemia, hypertriglyceridemia, hypo-high density lipoproteinemia, hyperlipemia, atherosclerosis and diseases derived therefrom (e.g. ischemic heart failure such as myocardial infarction, and cerebral vascular disorder such as cerebral infarction or cerebral apoplexy) in a mammal (e.g. mouse, rat, rabbit, dog, cat, cow, pig, monkey, human etc.).

The compound of the present invention can be preferably used for preventing primary occurrence and/or secondary occurrence of cardiovascular events (for example, (acute) coronary syndrome, cerebral infarction and the like) in high risk patients (patients having risks such as smoking, aging, gender (male), history or family history of hyperlipemia, diabetes, hypertension, myocardial infarction, angina, cerebral apoplexy and the like).

The present invention also provides an agent for regressing, suppressing progression of or stabilizing an arteriosclerotic lesion, which contains the present compound. Such an agent for regressing, suppressing progression of or stabilizing an arteriosclerotic lesion is preferably used in combination with a HMG-CoA reductase inhibitor.

The compound of the present invention can be also used as a prophylactic or therapeutic agent against Alzheimer's disease, multiple risk syndrome and metabolism syndrome.

Since the compound of the present invention is superior in absorbability after oral administration, it is preferable to be administered as oral preparation.

In treatment of these diseases, the compound of the present invention may be used alone or may be used in combination with other pharmaceutical components including other lipid lowering agents or cholesterol lowering agents, myocardial protecting agents, coronary disease treating agents, diabetes treating agents, thyroid dysfunction treating agents, nephrotic syndrome treating agents, osteoporosis treating agents and chronic renal failure treating agents. In this case, each of these compounds is preferably administered as an oral formulation or, if necessary, may be administered in a form of a suppository as a rectal formulation. In this case, examples of a possible component to be combined include fibrates [e.g. clofibrate, bezafibrate, gemfibrosil, fenofibrate, Wy-1463, GW9578 etc.], nicotinic acid, derivatives and analogues thereof [e.g. acipimox], probcol and analogues thereof, bile acid-binding resin [e.g. cholestyramine, cholestipol etc.], cholesterol absorption suppressing compounds [e.g. sitosterol, neomycin etc.], cholesterol biosynthesis inhibiting compounds [e.g. HMG-CoA reductase inhibitor such as lovastatin, simvastatin, pravastatin, fluvastatin, atorvastatin, pitavastatin, rosuvastatin etc.], squalene epoxidase inhibitors [e.g. NB-598 and analogues etc.], and HDL increasing agents due to inhibition of cholesterol ester transporting protein, cholesterol absorption inhibitors [e.g. ezetimibe], ileum bile acid transporter inhibitors [e.g. HMR-1453-A, S-8921], squalene synthase inhibitors [e.g. TAK-475].

Still other possible components to be combined are oxidosqualine-lanosterol cyclase, for example, a decalin derivative, an azadecalin derivative and an indane derivative.

In addition, when combining with:
diabetes treating agent [actos, losiglitazon, kinedak, penfill, humalin, euglucon, glimicron, daonil, novolin, monotard, insulins, glucobay, dimelin, rastinon, bacilcon, deamelin S, iszilins, biguanide agent]; thyroid dysfunction treating agent [dried thyroid gland (thyroid), levothyroxine sodium (thyradin-S), liothyronidin sodium (thyronine, Thyronamin);
nephrotic syndrome treating agent: prednisolone (predonine), prednisolone succinate sodium (predonine), methylprednisolone succinate sodium (Solu-Medrol), betamethasone (rinderon)]; vasodilators [dipyridamole (Persantin), dilazep dihydrochloride (comelian)]; chronic renal failure treating agent [diuretics [e.g. furosemide (Lasix), bumetanide (lunetoron), azosemide (diart)], depressor (e.g. ACE inhibitor (enalapril maleate (renivase)) and Ca antagonist (manidipine), α-receptor blocker, β-receptor blocker, angiotensin II receptor antagonist (candesartan cilexetil); an oral administration is preferred.

In view of lipid-rich plaque regressing activity and ACAT inhibitory activity, the compound of the present invention is suitable for preventing and treating thrombus formation. For this purpose, the compound of the present invention is administered alone or in combination with the following known treating agents, preferably via an oral route:
thrombus formation preventing or treating agent: anticoagulating inhibitor [e.g. heparin sodium, heparin potassium, warfarin potassium (warfarin), thrombin inhibitors (e.g. ximelagatran), FXa inhibitor], thrombolytic agent [e.g. tPA, urokinase], anti-platelet agent [e.g. aspirin, sulfinpyrazone (anturan), dipyridamole (persantin), ticlopidine (panaldine), cilostazol (pletaal), GPIIb/IIIa antagonist (ReoPro), clopidogrel];
coronary vasodilating agent: nifedipine, diltiazem, nicorandil, nitrous acid agent;
myocardial protecting agent: cardiac ATP-K opener, endothelin antagonist, urotensin antagonist, or the like.

The compound of the present invention may be also used, against the above-mentioned diseases, in combination with a biological preparation (e.g. antibody, vaccine preparation etc.) or as combined therapy in combination with genetic therapy or the like. Examples of the antibody and the vaccine preparation include, in addition to a vaccine preparation against angiotensin II, a vaccine preparation CETP, a CETP antibody, a TNF α antibody, an antibody against other cytokine, an amyloid β vaccine preparation, and 1-type diabetes vaccine (DIAPEP-277 of Peptor, etc.), an antibody or a vaccine preparation against cytokine, renin or angiotensin enzyme and a product thereof, an antibody or a vaccine preparation against an enzyme and a protein involved in blood lipid metabolism, an antibody or a vaccine against an enzyme and a protein involved in a coagulation or fibrinolysis system in blood, and an antibody or a vaccine preparation against a protein involved in saccharide metabolism or insulin resistance. Examples of genetic therapy include therapy using a gene relating to cytokine, a renin or angiotensin enzyme and a product thereof, therapy using DNA decoy such as NFκB decoy, therapy using antisense, therapy using RNA interference, therapy using a gene relating to an enzyme and a protein involved in blood lipid metabolism (e.g. gene relating to metabolism, excretion and absorption of cholesterol, triglyceride, HDL-cholesterol or blood phospholipid), therapy using a gene relating to an enzyme and a protein (e.g. growth factors such as HGF and VEGF) involved in vascularization therapy directed to peripheral vessel obstruction or the like, therapy using a gene relating to a protein involved in saccharide metabolism or insulin resistance, and antisense against cytokine such as TNF. Alternatively, the compound of the present invention can be also used in combination with vascularization therapy utilizing various organs regeneration such as heart regeneration, kidney regeneration, pancreas regeneration and vessel regeneration or transplantation of marrow cells (marrow mononuclear cell, marrow stem cell etc.).

The compound of the present invention can be used orally or parenterally by injection, drip, inhalation rectal administration or local administration and can be used as it is, or as a pharmaceutical composition (e.g. powders, granules, tablets, pills, capsules, injections, syrups, emulsions, elixirs, suspensions, solutions etc.). That is, at least one of the compounds of the present invention can be used alone, or as a mixture with a pharmaceutically acceptable carrier (adjuvant, excipient, additive, and/or diluent).

A pharmaceutical composition can be formulated according to a conventional method. Such a formulation can be usually prepared by mixing/kneading an active component with additives such as an excipient, a diluent, a carrier and the like. Herein, a parenteral administration includes subcutaneous injection, intravenous injection, intramuscular injection, intraperitoneal injection and dripping infusion. A formulation for injection, for example, a sterile injection aqueous suspension or oily suspension can be prepared using a suitable dispersing agent or wetting agent and a suspending agent by a method known in the art. The sterile formulation for injection may be a sterile injectable solution or suspension in a diluent or a solvent which is non-toxic and can be administered parenterally, such as an aqueous solution. Examples of an acceptable vehicle or solvent which can be used include water, Ringer's solution and isotonic saline. As a solvent or a suspending solvent, a aseptic non-volatile oil can be also used usually. For such purpose, any non-volatile oil or fatty acid can be used, including natural or synthetic or semi-synthetic fatty oil and fatty acid, as well as natural or synthetic or semi-synthetic mono- or di- or triglycerides.

A suppository for rectal administration can be prepared by mixing an active ingredient with a suitable non-stimulating additive, for example, a substance which is solid at a normal temperature but is liquid at the temperature of intestinal tract to melt in a rectum whereby releasing the active ingredient, such as cacao butter and polyethylene glycols.

It is also effective to combine with a suitable base (e.g. polymer of butyric acid, polymer of glycolic acid, copolymer of butyric acid-glycolic acid, a mixture of a polymer of butyric acid and a polymer of glycolic acid, polyglycerol fatty acid ester etc.) to obtain a sustained-release formulation.

Examples of a solid dosage form for oral administration include the aforementioned powders, granules, tablets, pills, and capsules. Formulation with such a dosage form can be prepared by mixing and/or kneading an active ingredient compound with at least one additive, for example, sucrose, lactose, cellulose, mannitol (D-mannitol), maltitol, dextran, starches (e.g. cornstarch), microcrystalline cellulose, agar, alginates, chitins, chitosans, pectins, tragacanth gums, gum arabic, gelatins, collagens, casein, albumin, synthetic or semi-synthetic polymers or glycerides. Such a dosage form can contain further additives as usual, including inert diluents, lubricants such as magnesium stearate, preservatives such as parabens and sorbic acid, antioxidant such as ascorbic acid, α-tocopherol and cysteine, disintegrants (e.g. croscarmellose sodium), binders (e.g. hydroxypropyl cellulose), thickening agents, buffering agents, sweeteners, flavoring agents and perfumes. Tablets and pills may be also enteric coated. Examples of oral liquid formulations include pharmaceutically acceptable emulsions, syrups, elixirs, suspensions and solutions, which may contain inert diluents which are conventionally used in the art, for example, water and, if necessary, additives. Such oral liquid formulations can be prepared by the conventional method, for example, by mixing an active ingredient, an inert diluent and, if necessary, other additives. An oral formulation usually contain about 0.01 to 99 W %, preferably about 0.1 to 90 W %, normally about 0.5 to 50 W % of the active ingredient compound of the present invention, though the amount may vary depending on the dosage form.

The dose for a certain patient is determined depending on the age, body weight, general condition, sex, diet, administration time, administration mode, excretion rate, drug combination, and a degree of the disease treated currently as well as other factors.

A lipid-rich plaque regressing agent containing the compound of the present invention is low toxic, and can be used safely. Its daily dose varies depending on the condition and body weight of a patient, the type of the compound, the administration route and the like and, for example, when used as a prophylactic or therapeutic agent against hyperlipemia, it may be about 1 to 500 mg, preferably about 10 to 200 mg as the compound represented by the formula [I] in an oral formulation, and about 0.1 to 100 mg, preferably about 1 to 500 mg, usually about 1 to 20 mg as the compound represented by the formula [I] in a parenteral formulation for an adult (about 60 kg). No toxicity is observed in these ranges.

The present invention also provides:
(1) a pharmaceutical composition comprising the compound of the present invention with a concomitant drug (hereinafter, abbreviated as a concomitant formulation),
(2) a method for regressing lipid-rich plaque or a method for inhibiting ACAT, which comprises administering a combination of an effective amount of the compound of the present invention and an effective amount of a concomitant drug to a mammal,
(3) a method for preventing or treating (acute) coronary syndrome such as myocardial infarction, unstable angina and the like; peripheral artery occlusion, restenosis after percutaneous coronary plasty (PTCA), restenosis after stent placement, atherosclerosis, myocardial infarction, ischemic heart failure such as angina, arteriosclerosis, intermittent claudication, cerebral vascular disorder such as cerebral apoplexy (e.g. cerebral infarction, cerebral embolus, cerebral hemorrhage), lacunar infarction, cerebral vascular dementia, Alzheimer's disease, multiple risk syndrome and metabolism syndrome, xanthomatosis, hyperlipemia, hypercholestorolemia, hypertriglyceridemia, hypo-high density lipoproteinemia) or thrombus formation, which comprises administering a combination of an effective amount of the compound of the present invention and an effective amount of a concomitant drug to a mammal, and
(4) a method for regressing, inhibiting progression of or stabilizing an arteriosclerotic lesion, which comprises administering a combination of an effective amount of the compound of the present invention and an effective amount of a concomitant drug to a mammal.

Examples of a concomitant drug which can be used with the compound of the present invention include the aforementioned pharmaceutical components other than the compound of the present invention and other hyperlipemia treating agent, a diuretic, a hypertension treating agent, a cardiac failure treating agent, an arrhythmia treating agent, an anticoagulant, an anti-platelet agent, a diabetes treating agent, a HDL increasing agent, an unstable plaque stabilizing agent, a vasodilator, an vasoconstrictor, a vasopressor, an antibacterial agent, an antifungal agent, non-steroidal antiinflammatory agent, a steroidal agent, an immunoregulator, an antiprotozoal agent, an anti-ulcer agent, an antitussive or expectorant, a sedative, an anesthetic, an antianxiety agent, an antipsychotic agent, a muscle relaxant, an antiepilepsy agent, an antidepressant, a narcotic antagonist, an anti-tumor agent, an anti-allergic agent, a vitamin, a vitamin derivative, a bone-calcium metabolizing agent, an osteoporosis treating agent, an arthritis treating agent, an anti-rheumatic agent, an anti-asthmatic agent, a pollakiuria or urine incontinence treating agent, a renal failure or nephropathy treating agent, an atopic dermatitis treating agent, an allergic rhinitis treating agent, an endotoxin antagonist or antibody, a signal transmission inhibitor, an inflammatory mediating effect inhibitor, an inflammatory mediating effect inhibiting antibody, an anti-inflammatory mediating effect inhibitor, and an anti-inflammatory mediating effect inhibiting agent. Inter alia, a hyperlipemia treating agent, a diuretic, a hypertension treating agent, a cardiac failure treating agent, an arrhythmia treating agent, an anti-coagulant, an anti-platelet agent, a diabetes treating agent, a HDL increasing agent, and an unstable plaque stabilizing agent are preferable. Examples of a concomitant drug other than the aforementioned pharmaceutical components are specifically listed below:

(1) Hyperlipemia Treating Agent

HMG-CoA reductase inhibitor (e.g. fluvastatin, cerivastatin, atorvastatin, simvastatin etc.), fibrates (e.g. simfibrate, clofibrate aluminium, clinofibrate, fenofibrate etc.), anion exchange resin (e.g. cholestyramide etc.), nicotinic acid formulation (e.g. nicomol, niceritrol, tocopherol nicotinate etc.), polyvalent unsaturated fatty acid derivative (e.g. ethyl icosapentate, polyene phosphatidylcholine, melinamide etc.), vegetable sterol (e.g. gamma-oryzanol, soysterol etc.), elastase, sodium dextran sulfate, squalene synthetase inhibitor, CETP inhibitor, cholesterol absorption inhibitors [e.g. ezetimibe], ileum bile acid transporter inhibitors [e.g. HMR-1453-A, S-8921], ethyl 2-chloro-3-[4-(2-methyl-2-phenylpropoxy)phenyl]propionate [Chem. Pharm. Bull], 38, 2792-2796 (1990)], PPARα agonists, PPARγ agonists, PPARδ agonists, LXR agonists, FXR antagonists, DGAT inhibitors, MGAT inhibitors, MTP inhibitors, and the like.

(2) Diuretic thiazide diuretic (benzylhydro-chorothiazide, cyclopenthiazide, ethiazide, hydrochlorothiazide, hydroflumethiazide, methylclothiazide, penfluthiazide, polythiazide, trichloromethiazide etc.), loop diuretic (chlortalidone, clofenamide, indapamide, mefruside, meticrane, sotolazone, tripamide, quinethazone, metolazole, furosemide, mefruside etc.), potassium retaining diuretic (spironolacton, triamterene etc.).

(3) Hypertension Treating Agent

[1] Sympathetic Nerve Suppressant
α$_2$ stimulant (e.g. clonidine, guanabenz, guanfacine, methyldopa etc.), ganglionic blocking agent (e.g. hexamethonium, trimethaphan etc.), presynaptic blocker (e.g. alseroxylon, dimethylaminoreserpinate, rescinamine, reserpine, syrosingopine etc.), neuron blocker (e.g. betanidine, guananethidine etc.), α$_1$ blocker (e.g. bunazosin, doxazocin, prazosin, terazosin, urapidil etc.), β blocker (e.g. propranolol, nadolol, timolol, nipradilol, bunitrolol, indenolol, penbutolol, carteolol, carvedilol, pindolol, acebutolol, atenolol, bisoprolol, metoprolol, labetalol, amosulalol, arotinolol etc.).

[2] Vasodilator
calcium channel antagonist (e.g. manidipine, nicardipine, nilvadipine, nisoldipine, nitrendipine, benidipine, amlodipine, aranidipine etc.), phthalazine derivative (e.g. budralazine, cadralazine, ecarazine, hydralazine, todralazine etc.).

[3] ACE Inhibitor
alacepril, captopril, cilazapril, delapril, enalapril, lisinopril, temocapril, trandolapril, quinapril, imidapril, benazepril, perindopril etc.

[4] Angiotensin II Receptor Antagonist
losartan, candesartan cilexetil, valsartan, telmisartan, irbesartan, forasartan, olmesartan medoxomil, 2-ethoxy-1-{[2'-(5-oxo-4,5-dihydro-1,2,4-oxadiazol-3-yl)biphenyl-4-yl]methyl}-1H-benzimidazole-7-carboxylic acid etc.

[5] Diuretic (e.g. the aforementioned diuretics)

[6] β-blocker (e.g. propranolol, alprenolol, bufetolol, oxprenolol, atenolol, acebutolol, metoprolol, bisoprolol, pindolol, carteolol, arotinolol etc.

(4) Cardiac Failure Treating Agent cardiotonic agent (e.g. digitoxin, digoxin, methyldigoxin, lanatoside C, proscillaridine), α,β-stimulant (e.g. epinephrine, norepinephrine, isoproterenol, dopamine, docarpamine, dobutamine, denopamine etc.), phosphodiesterase inhibitor (e.g. amrinone, milrinone, olprinone hydrochloride etc.), calcium channel sensitivity promoter (e.g. pimobendan etc.), nitrate agent (e.g. nitroglycerin, isosorbide nitrate etc.), ACE inhibitor (e.g. the aforementioned ACE inhibitors etc.), diuretic (e.g. the aforementioned diuretics etc.), carperitide, ubidecarenone, vesnarinone, aminophylline etc.).

(5) Arrhythmia Treating Agent sodium channel blocker (e.g. quinidine, procainamide, disopyramide, ajimaline, cibenzoline, lidocaine, diphenyl hydantoin, mexiletine, propafenone, flecainide, pilsicanide, phenyloin etc.), β-blocker (e.g. propranolol, alprenolol, bufetolol, oxprenolol, atenolol, acebutolol, metoprolol, bisoprolol, pindolol, carteolol, arotinolol etc.), potassium channel blocker (e.g. amiodarone etc.), calcium channel blocker (e.g. verapamil, diltiazem etc.) etc.

(6) Anticoagulant and Antiplatelet Agent sodium citrate, activated protein C, tissue factor pathway inhibitor, anti-thrombin III, dalteparin sodium, argatroban, gabexate, sodium ozagrel, ethyl icosapentate, beraprost sodium, alprostadil, pentoxifylline, tisokinase, streptokinase, heparin sodium, heparin potassium, warfarin potassium (warfarin), thrombin inhibitors (e.g. ximelagatran), FXa inhibitor], thrombolytic agent [e.g. tPA, urokinase], anti-platelet agent [e.g. aspirin, sulfinpyrazone (anturan), dipyridamole (persantin), ticlopidine (panaldine), cilostazol (pletaal), GPIIb/IIIa antagonist (ReoPro), clopidogrel] etc.

(7) Diabetes Treating Agent sulfonyl urea (e.g. tolbutamide, chlorpropamide, glycopyramide, acetohexamid, tolazamide, glibenclamide, glybuzole etc.), biguanide (e.g. metformin hydrochloride, buformin hydrochloride etc.), α-glucosidase inhibitor (e.g. voglibose, acarbose etc.), insulin sensitizer (e.g. pioglitazone, troglitazone, rosiglitazone etc.), insulin, glucagon, diabetic complication treating agent (e.g. epalrestat etc.) etc.

(8) HDL Increasing Agent squalene synthetase inhibitor, CETP inhibitor, LPL activator, endothelial lipase inhibitor etc.

(9) Unstable Plaque Stabilizing Agent

MMP inhibitor, kinase inhibitor etc.

(10) Vasodilator oxyphedrine, diltiazem, tolazoline, hexobendine, bamethan, clonidine, methyldopa, guanabenz etc.

(11) Vasoconstrictor dopamine, dobutamine, denopamine etc.

(12) Hypertensive Agent dopamine, dobutamine, denopamine, digitoxin, digoxin, methyldigoxin, lanatoside C, G-Strophantin etc.

(13) Antibacterial Agent

[1] Sulfonamide
sulfamethizole, sulfisoxazole, sulfamonomethoxin, sulfamethizole, salazosulfapyridine, silver sulfadiazine etc.

[2] Quinolone
nalidixic acid, pipemidic acid trihydrate, enoxacin, norfloxacin, ofloxacin, tosufloxacin, tosilate, ciprofloxacin hydrochloride, lomefloxacin hydrochloride, sparfloxacin, fleroxacin etc.

[3] Anti-Tuberculous Agent isoniazid, ethambutol (ethambutol hydrochloride), p-aminosalicylic acid (calcium p-aminosalicylate), pyrazinamide, ethionamide, prothionamide, rifampicin, streptomycin sulfate, kanamycin sulfate, cycloserine etc.

[4] Anti Acid-Fast Bacteria Agent diaphenylsulfone, rifampicin etc.

[5] Anti-Viral Agent idoxuridine, acyclovir, vidarabine, ganciclovir etc.

[6] Anti-HIV Agent zidovudine, didanosine, zalcitabine, indinavir sulfate ethanol adduct, ritonavir etc.

[7] Anti-Spirochete Agent

[8] Antibiotic tetracyclin hydrochloride, ampicillin, piperacillin, gentamycin, dibekacin, kanendomycin, lividomycin, tobramycin, amikacin, fradiomycin, sisomicin, tetracyclin, oxytetracyclin, rolitetracyclin, doxycyclin, ampicillin, piperacillin, ticarcillin, cefalotin, cefapirin, cefaloridine, cefaclor, cefalexin, cefroxadine, cefadroxil, cefamandole, cefotoam, cefroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazon, ceftizoxime, moxalactam, thienamycin, sulfazecin, azthreonam or a salt thereof, griseofulvin, lankacidin [J. Antibiotics, 38, 877-885(1985)] etc.

(14) Antifungal Agent

[1] Polyethylene-based antibiotic (e.g. amphotericin B, nystatin, trichomycin)

[2] Griseofulvin, pyrrolnitrin etc.

[3] Cytosine metabolism antagonist (e.g. flucytosine)

[4] Imidazole derivative (e.g. econazole, clotrimazole, miconazole nitrate, bifonazole, croconazole)

[5] Triazole derivative (e.g. fluconazole, itraconazole, azole-based compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl-3-(2H,4H)-1,2,4-triazolone]

[6] Thiocarbamic acid derivative (e.g. trinaphthol)

[7] Echinocandin-based derivative (e.g. caspofamgine, FK-463, V-Echinocadin) etc.

(15) Non-Steroidal Antiinflammatory Agent acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprodin, flurbiprofen, fenbufen, pranoprofen, floctafenine, epirizol, tiaramide hydrochloride, zaltoprofen, gabexate mesilate, camostat mesilate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone or a salt thereof.

(16) Steroidal Agent dexamethasone, hexestrol, methimazole, betamethasone, triamcinolone, triamcinolone acetonide, fluorocinonide, fluorocinolone acetonide, prednisolone, methylprednisolone, cortisone acetate, hydrocortisone, fluorometholone, beclometasone dipropionate, estriol etc.

(17) Immunoregulating Agent cyclosporin, tacrolimus, gusperimus, azathioprine, antilymph serum, dried sulfonated-immunogloburin, erythropoietin, colony stimulating factor, interleukin, interferon etc.

(18) Antiprotozoal Agent metronidazole, tinidazole, diethylcarbamadine citrate, quinine hydrochloride, quinine sulfate etc.

(19) Anti-Ulcer Agent metoclopramide, histidine hydrochloride, lansoprazole, metoclopramide, pirenzepine, cimetidine, ranitidine, famotidine, urogastrine, oxethazaine, proglumide, omeprazole, sucralfate, sulpiride, cetraxate, gefarnate, aldioxa, teprenone, prostaglandin etc.

(20) Bronchospasmolytic Expectorant ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, aroclamide, chlorfesianol, picoperidamine, cloperastine, protokylol, isoproterenol, salbutamol, terbutaline, oxymetebanol, morphine hydrochloride, dextromethorphan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethylcysteine hydrochloride, carbocysteine etc.

(21) Sedative chlorpromazine hydrochloride, atropine sulfate, phenobarbital, barbital, amobarbital, pentobarbital, thiopental sodium, thiamylal sodium, nitrazepam, estazolam, flunitrazepam, haloxazolam, triazolam, flunitrazepam, bromovalerylurea, chloral hydrate, triclofos sodium etc.

(22) Anesthetic (22-1) Local Anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine etc.

(22-2) Systemic Anesthetic

[1] Inhalation anesthetic (e.g. ether, halothane, nitrous oxide, enflurane, enflurane),

[2] Intravenous anesthetic (e.g. ketamine, droperidol, thiopental sodium, thiamylal sodium, pentobarbital) etc.

(23) Anxiolytic Agent diazepam, lorazepam, oxazepam, clordiazepoxide, medazepam, oxazolam, cloxazolam, clotiazepam, prazepam, etizolam, fludiazepam, hydroxyzine etc.

(24) Antipsychotic Agent chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clomipramine hydrochloride, sulpiride, zotepine etc.

(25) Muscle Relaxant pridinol, tubocurarine, pancuronium, tolperisone hydrochloride, chlorphenesin carbamate, baclofen, chlormezanone, mephenesin, chlozoxazone, eperisone, tizanidine, etc.

(26) Antieptileptic Agent phenyloin, ethosuximide, acetazolamide, chlordiazepoxide, trimethadione, carbamazepine, phenobarbital, primidone, sulthiam, sodium valproate, clonazepam, diazepam, nitrazepam etc.

(27) Antidepressant imipramine, clomipramine, noxiptiline, pheneridine, amitriptyline hydrochloride, nortriptyline, amoxapine, mianserin hydrochloride, maprotiline hydrochloride, sulpiride, fluvoxamine maleate, trazodone hydrochloride etc.

(28) Anesthetic Antagonist levallorphan, nalorphine, naloxone or a salt thereof etc.

(29) Antitumor Agent

6-O—(N-Chloroacetylcarbamoyl), fumagilol, bleomycin, methotrexate, actinomycin D, mitomycin C, daunorubicin, adriamycin, neocarcinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, zisulphan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, clormadinone acetate, leuproreline acetate, buserelin acetate etc.

(30) Anti-Allergic Agent diphenhydramine, chlorphenyramine, tripelennamine, methodiramine, clemizole, diphenylpyraline, methoxyphenamine, sodium cromoglicate, tranilast, repirinast, amlexanox, ibudilast, ketotifen, terfenadine, mequitazine, azelastine, epinastine, ozagrel hydrochloride, pranlukast hydrate, seratrodast, etc.

(31) Lipid-Soluble Vitamin

[1] Vitamin A: vitamin $A_1$, vitamin $A_2$ and retinol palmitate

[2] Vitamin D: vitamin $D_1$, $D_2$, $D_3$, $D_4$ and $D_5$

[3] Vitamin E: $\alpha$-tocopherol, $\beta$-tocopherol, $\gamma$-tocopherol, $\delta$-tocopherol, dl-$\alpha$-tocopherol nicotinate

[4] Vitamin K: vitamin $K_1$, $K_2$, $K_3$ and $K_4$

[5] Folic acid (vitamin M) etc.

(32) Vitamin Derivative various vitamin derivatives, for example, vitamin $D_3$ derivative including 5,6-trans-cholecalciferol, 2,5-hydroxycholecalciferol and 1-$\alpha$-hydroxycholecalciferol, vitamin $D_2$ derivative including 5,6-trans-ergocalciferol etc.

(33) Anti-Asthmatic Agent isoprenaline hydrochloride, salbutamol sulfate, procaterol hydrochloride, terbutaline sulfate, trimetoquinol hydrochloride, tubobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlukast hydrate, seratrodast, dexamethasone, prednisolone, hydrocortisone, beclometaason dipropionate etc.

(34) Pollakiuria or Urine Incontinence Treating Agent flavoxate hydrochloride etc.

(35) Atopic Dermatitis Treating Agent sodium cromoglicate etc.

(36) Allergic Rhinitis Treating Agent sodium cromoglicate, chlorphenyramine maleate, alimemazine tartrate, clemastine fumarate, homochlorcyclizine hydrochloride, terfenadine, mequitazine etc.

(37) Dementia Treating Agent acetylcholine estrase inhibitor (e.g. donepezil, tacrine, rivastigmine, galanthamine etc.) etc.

(38) Others hydroxycam, diaserine, megestrol acetate, nicergoline, prostaglandins etc.

By means of a combination of the compound of the present invention with a concomitant drug, for example, the following effects are exerted.

(1) The dose or side effects of the compound of the present invention or a concomitant drug can be lower than those when given alone.

(2) A synergistic therapeutic effect can be obtained against diseases such (acute) coronary syndrome such as myocardial infarction and unstable angina, peripheral artery occlusion, intermittent claudication, restenosis after percutaneous coronary plasty (PTCA), restenosis after stent placement, hypercholestorolemia, hypertriglyceridemia, hyperlipemia, hypo-high density lipoproteinemia, atherosclerosis, myocardial infarction, ischemic heart failure such as angina, cerebral vascular disorder such as cerebral apoplexy or cerebral infarction, lacunar infarction, cerebral vascular dementia, xanthomatosis, Alzheimer's disease, thrombus formation or the like.

(3) A wide therapeutic effect can be obtained against various diseases accompanied with diseases such as (acute) coronary syndrome such as myocardial infarction, unstable angina, peripheral artery occlusion, intermittent claudication, restenosis after percutaneous coronary plasty (PTCA), restenosis after stent placement, hypercholestorolemia, hypertriglyceridemia, hyperlipemia, hypo-high density lipoproteinemia, atherosclerosis, myocardial infarction, ischemic heart failure such as angina, cerebral vascular disorder such as cerebral apoplexy or cerebral infarction, lacunar infarction, cerebral vascular dementia, xanthomatosis, Alzheimer's disease, thrombus formation or the like.

When using the concomitant formulation of the present invention, the timing of administering the compound of the present invention and a concomitant drug are is limited, and the compound of the present invention or its pharmaceutical composition and a concomitant drug or its pharmaceutical composition may be administered at the same time, or may be administered at a certain time interval to a subject. The dose of a concomitant drug may be in accordance with to a clinically used dose, and can be appropriately selected depending on an administration subject, an administration route, disease, a combination and the like.

The administration mode of the concomitant formulation of the present invention is not particularly limited, and it is enough that the compound of the present invention and a concomitant drug are combined upon administration. Examples of such administration mode include (1) administration of a single formulation obtained by formulating the compound of the present invention and a concomitant drug simultaneously, (2) simultaneous administration of two formulations obtained by formulating the compound of the present invention and a concomitant drug separately, via an identical route, (3) sequential and intermittent administration of two formulations obtained by formulating the compound of the present invention and a concomitant drug separately, via an identical route, (4) simultaneous administration of two formulations obtained by formulating the compound of the present invention and a concomitant drug separately, via different routes, (5) sequential and intermittent administration of two for mualtions obtained by formulating the compound of the present invention and a concomitant drug separately, via different routes (e.g. the compound of the present invention or its pharmaceutical composition followed by a concomitant drug or its pharmaceutical composition, or inverse order) and the like.

The concomitant formulation of the present invention is low toxic, and thus the compound of the present invention and/or a concomitant drug describe above are mixed with a pharmacologically acceptable carrier according to a method known per se to form a pharmaceutical composition such as tablets (including sugar-coated tablets and film coating tablets), powders, granules, capsules (including soft capsules), solutions, injections, suppositories, sustained-release formulations and the like, which can be safely given orally or parenterally (e.g. topically, rectally, intravenously). Injections can be administered intravenously, intramuscularly, subcutaneously, into organs, or directly into lesions.

Examples of the pharmacological acceptable carrier which may be used in preparing the concomitant formulation of the present invention include various organic or inorganic carrier materials which are conventionally used as pharmaceutical materials, for example, excipients, lubricants, binders and disintegrants in a solid formulation, or solvents, dissolution aids, suspending agents, isotonizing agents, buffering agents and soothing agents in a liquid formulation. Further, if necessary, usual additives such as preservatives, antioxidants, coloring agents, sweeteners, adsorbents, wetting agents and the like may be conveniently added in suitable amounts.

The ratio between the compound of the present invention and a concomitant drug in the concomitant formulation of the present invention may be selected appropriately depending on an administration subject, an administration route, disease and the like.

For example, the content of the compound of the present invention in the concomitant formulation of the present invention varies depending on the dosage form, and is usually about 0.01 to 100% by weight, preferably about 0.1 to 50% by weight, more preferably about 0.5 to 20% by weight of the entire formulation.

The content of a concomitant drug in the concomitant formulation of the present invention varies depending on the dosage form, and is usually about 0.01 to 100% by weight, preferably about 0.1 to 50% by weight, more preferably about 0.5 to 20% by weight of the entire formulation.

The content of additives such as a carrier and the like in the concomitant formulation of the present invention varies depending on the dosage form, and is usually about 1 to 99.99% by weight, preferably about 10 to 90% by weight of the entire formulation.

In addition, the same content may be used also when the compound of the present invention and a concomitant drug are formulated separately.

Such a formulation can be prepared by a method known per se which is used generally in a pharmaceutical process.

The dose of the concomitant formulation of the present invention varies depending on the kind of the compound of the present invention, age, body weight, symptom, dosage form, administration method, administration period and the like. For example, the daily dose for a hyperlipemia patient (adult, about 60 kg) is usually about 0.01 to about 100 mg/kg, preferably about 0.01 to about 100 mg/kg, more preferably about 0.1 to about 100 mg/kg, particularly about 0.1 to about 50 mg/kg, inter alia, about 1.5 to about 30 mg/kg of the compound of the present invention and administered intravenously once or in several portions. Of course, since a dose varies depending on various conditions as described above, an amount smaller than the aforementioned dose may be sufficient or a dose exceeding the aforementioned range may be necessary.

The dose of a concomitant drug can be set in any range as far as it does not cause problematic side effect. The daily dose of a concomitant drug is not limited particularly and varies depending on the severity of symptom, age, sex, body weight and susceptibility of a subject to be administered, timing and interval of administration, nature, preparation and kind of a pharmaceutical formulation, kind of an active ingredient, and the like. The daily oral dose per kg body weight in a mammal is usually about 0.001 to 2000 mg, preferably about 0.01 to 500 mg, further preferably about 0.1 to 100 mg of a concomitant drug, which is given usually in 1 to 4 portions.

Upon administration of the concomitant formulation of the present invention, the compound of the present invention and a concomitant drug may be administered at the same time, but after a concomitant drug is administered, the compound of the present invention may be administered. Alternatively, after the compound of the present invention is administered, a concomitant drug may be administered. When they are administered at a certain time interval, the interval varies depending on an active ingredient to be administered, a dosage form, an administration method and the like. For example, when a concomitant drug is administered in advance, the compound of the present invention is administered in 1 minute to 3 days, preferably minutes, to 1 day, more preferably 15 minute to 1 hour after administration of a concomitant drug. For example, when the compound of the present invention is administered in advance, a concomitant drug is administered in 1 minute to 1 day, preferably 10 minutes to 6 hours, more preferably 15 minutes to 1 hour after administration of the compound of the present invention.

As a preferable administration method, for example, about 0.001 to 200 mg/kg of a concomitant drug which has been formulated into an oral formulation is orally administered and, after about 15 minutes, about 0.005 to 100 mg/kg of the compound of the present invention which has been formulated into an oral formulation is orally administered as the daily dose.

The compound of the present invention possesses excellent lipid-rich plaque regressing activity or/and ACAT inhibitory activity.

The following Examples, Formulation Examples and Experimental Examples further illustrate the present invention, but the present invention is not limited by them.

A $^1$H-NMR spectrum was measured with a Varian Mercury 300 (300 MHz) spectrometer using tetramethylsilane as an internal standard, and each δ values are represented in ppm. The X-ray powder diffraction was measured by using RIGAKU RINT2100Ultima+ (CuKα-ray (λ=1.5418 Å)). Unless otherwise is indicated, a numerical value shown for a mixed solvent is a volume ratio of each solvent. Unless otherwise indicated, % means % by weight. In addition, the ratio of an eluted solvent for silica gel column chromatography indicates a volume ratio, unless otherwise indicated. Herein, room temperature (normal temperature) represents a temperature of about 20° C. to about 30° C.

Respective symbols in Examples represent the following meanings.

Et: ethyl, Bu: butyl, DBU: diazabicycloundecene, s: singlet, d: doublet, t: triplet, q: quartet, quint: quintet, sext; sextet, dd: double doublet, dt: double triplet, m: multiplet, br: broad, J: coupling constant.

REFERENCE EXAMPLE 1

(3-Bromophenyl)(4-chloro-2-hydroxy-5-methylphenyl)methanone

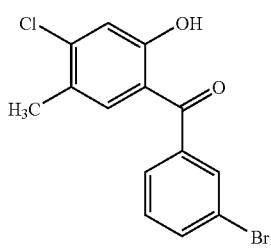

Aluminum chloride (20.4 g) was added to a solution of 3-chloro-4-methylanisole (20 g) in chlorobenzene (56 ml) at 20-30° C., and then 3-bromobenzoyl chloride (28 g) was further added dropwise over about 30 minutes at 25 to 30° C. After completion of addition, the mixture was stirred at 25° C. for 1 hour, and then heated at 40° C. for 1 hour. After the reaction was completed, the mixture was cooled, and toluene/tetrahydrofuran (1:1, 200 ml) was added dropwise at 20 to 30° C. Then, 4N hydrochloric acid (80 ml) was added dropwise. The organic layer was separated, washed successively with 2N hydrochloric acid (60 ml) and a 10% aqueous sodium chloride solution. The organic layer was concentrated to 80 g. After methanol (100 ml) was added, the mixture was concentrated again to 90 g. Methanol (80 ml) was added to the residue, the mixture was stirred at room temperature for 30 minutes, and below 5° C. for 1 hour. Crystals were collected, washed with cooled methanol (40 ml) and dried under reduced pressure to obtain the title compound (35.4 g, yield 85.1%).

$^1$H-NMR (300 MHz, CDCl$_3$) δ (ppm): 2.28 (3H, s), 7.12 (1H, s), 7.36-7.42 (2H, m), 7.54-7.57 (1H, m), 7.72-7.80 (2H, m), 11.7 (1H, s).

REFERENCE EXAMPLE 2

Ethyl[4-(3-bromophenyl)-7-chloro-6-methyl-2-oxo-2H-chromen-3-yl]acetate

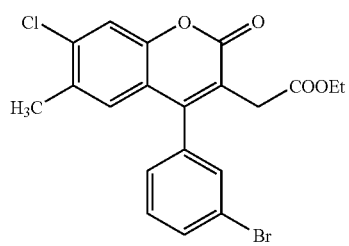

DBU (211 ml) was added to a solution of (3-bromophenyl)(4-chloro-2-hydroxy-5-methylphenyl)methanone (170 g) in acetonitrile (510 ml) at 25 to 30° C. Then, a solution of ethyl succinate chloride (146 g) in acetonitrile (340 ml) was added dropwise over 30 minutes at 25 to 40° C. After the drop was completed, the mixture was stirred at 30° C. for 1 hour. Water (94 ml) was added dropwise keeping the reaction solution at 25 to 30° C. After the mixture was stirred at the same temperature for 1 hour, the resulting crystals were filtered, and washed with a mixture of acetonitrile and water (9/1, 170 ml) four times, dried under reduced pressure to obtain the title compound (174 g, yield 76.7%).

$^1$H-NMR (300 MHz, CDCl$_3$) δ (ppm): 1.24 (3H, t, J=7.2 Hz), 2.30 (3H, s), 3.35 (2H, s), 4.14 (2H, q, J=7.2 Hz), 6.80 (1H, s), 7.20-7.23 (1H, s), 7.42-7.45 (3H, m), 7.65-7.68 (1H, m).

REFERENCE EXAMPLE 3

[4-(3-bromophenyl)-7-chloro-6-methyl-2-oxo-2H-chromen-3-yl]acetic acid

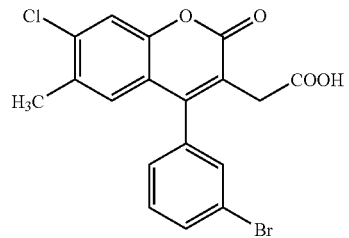

2N NaOH (51.6 ml) was added to a mixture of ethyl[4-(3-bromophenyl)-7-chloro-6-methyl-2-oxo-2H-chromen-3-yl]acetate (15 g) and ethanol (135 ml), and the mixture was stirred at 70° C. for 1 hour. After the mixture was cooled to 25° C., pH was adjusted to 2.0 by adding 6N HCl (17.7 ml) dropwise at the same temperature to make crystals precipitate. After the mixture was stirred at 25° C. for 1 hour, crystals were collected, washed with ethanol/water (2/1, 30 ml) and dried under reduced pressure to obtain the title compound (13.5 g, yield 96.4%).

$^1$H-NMR (300 MHz, CDCl$_3$) δ (ppm): 2.31 (3H, s), 3.35 (2H, s), 6.81 (1H, s), 7.24-7.27 (1H, s), 7.41-7.47 (3H, m), 7.65-7.69 (1H, m).

REFERENCE EXAMPLE 4

2-[4-(3-Bromophenyl)-7-chloro-6-methyl-2-oxo-2H-chromen-3-yl]-N-[4-fluoro-2-(trifluoromethyl)phenyl]acetamide

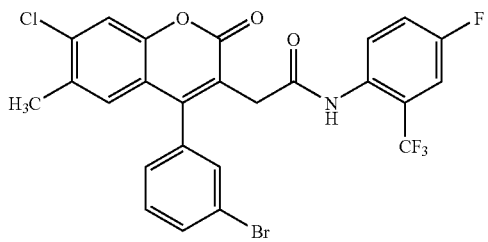

N,N-Dimethylformamide (0.2 ml) was added to a solution of [4-(3-bromophenyl)-7-chloro-6-methyl-2-oxo-2H-chromen-3-yl]acetic acid (13.5 g) in tetrahydrofuran (135 ml), and then thionyl chloride (5.12 g) was added dropwise to the resulting mixture with passing nitrogen through the reaction vessel at 25° C. After completion of the addition, the mixture was warmed to 40° C. and stirred for 1.5 hours. Then, 2-amino-5-fluorobenzotrifluoride (6.53 g) was added thereto, and the mixture was warmed to 60° C. and then stirred for 2.5 hours. Acetonitrile (67.5 ml) and water (67.5 ml) were added dropwise successively thereto at 40 to 50° C. The resulting mixture was stirred at 40° C. for 1 hour and at 5° C. for 1 hour. Crystals precipitated was collected by filtration, and washed with cold tetrahydrofuran/acetonitrile/water (2/1/1, 40.5 ml). The resulting crystals (17.3 g) were dissolved in acetone (173 ml) by heating. Activated charcoal (0.865 g) was added to the solution, and the mixture was stirred for 10 minutes. The activated charcoal was removed by filtration, and washed with acetone (86.5 ml). The combined filtrate and washings were kept at 40° C., and water (51.9 ml) was added dropwise thereto with stirring. The mixture was cooled to 5° C. and stirred for 1 hour. Crystals were collected by filtration and washed with cold acetone/water (5/1, 51.9 ml) to obtain the title compound (16.1 g, yield 85.7%).

$^1$H-NMR (300 MHz, CDCl$_3$) δ (ppm): 2.31 (3H, s), 3.35-3.52 (2H, m), 6.85 (1H, s), 7.19-7.32 (3H, m), 7.41-7.50 (3H, m), 7.67-7.69 (1H, m), 7.94-7.99 (1H, m), 8.11 (1H, brs).

REFERENCE EXAMPLE 5

Butyl(2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylate

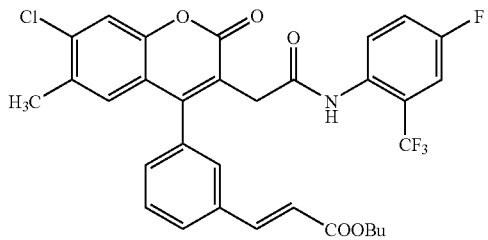

A mixture of 2-[4-(3-bromophenyl)-7-chloro-6-methyl-2-oxo-2H-chromen-3-yl]-N-[4-fluoro-2-(trifluoromethyl)phenyl]acetamide (2.00 g), palladium acetate (0.0079 g) and tri-o-tolyl phosphine (0.0214 g) was placed in a reaction vessel, and nitrogen was passed through the reaction vessel for 10 minutes to replace the atmosphere of the reaction vessel with nitrogen. N,N-Dimethylformamide (10 ml), butyl acrylate (0.677 g) and sodium acetate (0.317 g) were added successively thereto, and the mixture was stirred at room temperature for about 20 minutes. Then, the mixture was stirred at 110° C. for 3 hours and cooled to room temperature. Ethyl acetate (20 ml) and water (20 ml) were poured to the reaction mixture and, after stirring, an organic layer was separated. The organic layer was washed successively with a mixture of 10% saline (18 ml) and conc. hydrochloric acid (2 ml), and 10% saline (20 ml). Activated charcoal (0.1 g) and tributyl phosphine (0.0712 g) were added to the organic layer, and the mixture was stirred at room temperature for 10 minutes. Then, the activated charcoal was removed by filtration and washed with ethyl acetate (4 ml). The combined filtrate and washings were concentrated to 6.0 g under reduced pressure, and n-heptane (12 ml) was added dropwise to the residue to precipitate crystals. After stirring at 5° C. for 1 hour, the crystals were collected by filtration and washed with cold ethyl acetate/n-heptane (1/3, 4 ml). A mixture of the resulting crystals (2.06 g) and acetone (10 ml) were heated to 50° C. to dissolve the mixture, activated charcoal (0.1 g) was added thereto, and the mixture was stirred for 10 minutes. The activated charcoal was removed by filtration, and washed with acetone (4 ml). Water (4.6 ml) was added dropwise to the combined filtrate and washings, and the mixture was stirred at 5° C. for 1 hour. Crystals were collected by filtration, and washed with cold acetone/water (2/1, 4 ml) to obtain the title compound (1.84 g, yield 84.9%).

$^1$H-NMR (300 MHz, CDCl$_3$) δ(ppm): 0.95 (3H, t, J=7.4 Hz), 1.42 (2H, sext, J=7.4 Hz), 1.68 (2H, quint, J=6.7 Hz), 2.29 (3H, s), 3.39-3.50 (2H, m), 4.20 (2H, t, J=6.6 Hz), 6.50 (1H, d, J=16 Hz), 6.86 (1H, s), 7.19-7.32 (3H, m), 7.35 (1H, s), 7.44 (1H, s), 7.56-7.61 (1H, m), 7.69-7.74 (2H, m), 7.98-8.01 (1H, m), 8.17 (1H, brs).

REFERENCE EXAMPLE 6

(2E)-3-{3-[7-Chloro-3-(2-{[4-fluoro-2-(trifluoromethyl)phenyl]amino}-2-oxoethyl)-6-methyl-2-oxo-2H-chromen-4-yl]phenyl}acrylic acid acetone solvate

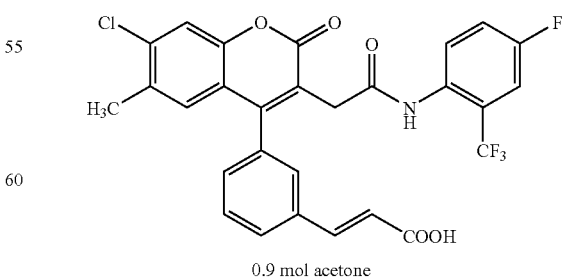

0.9 mol acetone

A mixture of butyl(2E)-3-{3-[7-chloro-3-(2-{[4-fluoro-2-(trifluoromethyl)phenyl]amino}-2-oxoethyl)-6-methyl-2- oxo-2H-chromen-4-yl]phenyl}acrylate (3.0 g), ethanol (9 ml) and 2N NaOH (9 ml) was stirred at 50° C. for 1.5 hours. After completion of the reaction, acetone (27 ml) was added to the reaction mixture at 50° C., and 6N HCl (3.5 ml) was added dropwise thereto to adjust pH to 0.6. The mixture was stirred at 50° C. for 30 minutes and then at 25° C. for 1 hour, and crystals were collected by filtration, and washed with acetone/water (2/1, 6 ml). To a mixture of the resulting crystals (2.79 g), acetone (2 ml) and water (6 ml) was added dropwise 5% aqueous ammonia (2.1 ml) with stirring at room temperature to adjust pH to 9.2 and dissolve the mixture. Toluene (4.5 ml) was added to the resulting solution and the mixture was stirred for 5 minutes and allowed to stand for 5 minutes to separate an aqueous layer. Acetone (12 ml) and activated charcoal (0.15 g) were added to the obtained aqueous layer and the mixture was stirred at room temperature for 15 minutes. The activated charcoal was removed by filtration, and washed with acetone (6 ml). The filtrate and washings were combined and warmed to 50° C., and 6N HCl (1.25 ml) was added dropwise thereto with keeping the temperature almost the same and stirring to adjust pH to 0.5 and precipitate crystals. The mixture was stirred at 50° C. for 30 minutes and then at about 25° C. for 1 hour, and the crystals were collected by filtration and washed with acetone/water (2/1, 6 ml) to obtain the title compound (2.54 g, yield 84.8%). This product contained 0.9 mol of acetone.

$^1$H-NMR (300 MHz, CDCl$_3$) δ(ppm): 2.07 (6H×0.9, s), 2.29 (3H, s), 3.38-3.51 (2H, m), 6.43 (1H, d, J=16 Hz), 6.85 (1H, s), 7.24-7.38 (3H,m), 7.46 (1H, s), 7.50 (1H, s), 7.57-7.62 (1H, m), 7.69-7.75 (2H, m), 7.97-8.01 (1H, m), 8.15 (1H, brs).

REFERENCE EXAMPLE 7

Sodium(2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylate

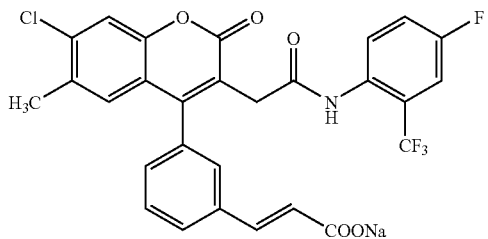

A mixture of (2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylic acid acetone solvate (1.13 g) and acetone (20.5 ml) was heated to 50° C., and 2N NaOH (0.91 ml) was added dropwise thereto with stirring. The mixture was stirred at 50° C. for 2 hours and then at 5° C. for 1 hour, and crystals precipitated were collected by filtration. The crystals were washed successively with cold acetone/water (95/5, 2 ml) and cold acetone (2 ml) to obtain the title compound (0.974 g, yield 91.9%).

$^1$H-NMR (300 MHz, DMSO-d$_6$) δ(ppm): 2.23 (3H, s), 3.37 (2H, br), 6.44 (1H, d, J=16 Hz), 6.94 (1H, s), 7.13 (1H, d, J=16 Hz), 7.20-7.22 (1H, m), 7.36-7.43 (2H, m), 7.52-7.61 (3H, m), 7.67-7.69 (2H, m), 9.70 (1H, brs).

EXAMPLE 1

Monocalcium bis((2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylate)•trihydrate

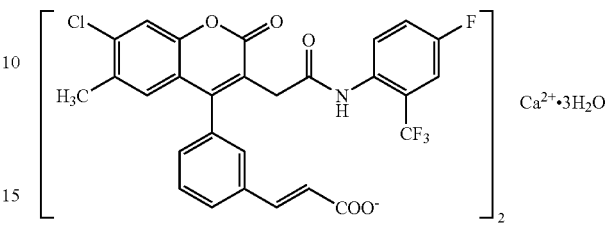

A mixture of sodium(2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylate (5.0 g), ethanol (45 ml) and water (9 ml) were dissolved by heating to 60° C. Impurities in the solution were removed by filtration and washed with warmed ethanol/water (5/1, 6 ml). A solution of calcium chloride (0.524 g) in water (10 ml) was added dropwise to the combined filtrate and washings with stirring at 60° C. The mixture was stirred at 60° C. for 3 hours and then at 25° C. for 1 hour. Crystals were collected by filtration, and washed successively with ethanol/water (1/1, 10 ml) and water (10 ml, three times) to obtain the title compound as colorless crystals (4.47 g, yield 89.8%). The crystals obtained show the X-ray powder diffraction pattern as shown in FIG. 1 and crystallinity was 66%.

$^1$H-NMR (300 MHz, DMSO-d$_6$) δ(ppm): 2.17 (3H, s), 3.32 (2H, br), 6.47 (1H, d, J=16 Hz), 6.87 (1H, s), 7.21-7.23 (1H, m), 7.32-7.54 (6H, m), 7.66 (2H, s), 9.65 (1H, brs).

The variation of the hydration number of the title compound in the range of monohydrate to tetrahydrate was observed depending upon humidity.

EXAMPLE 2

Figure 2:
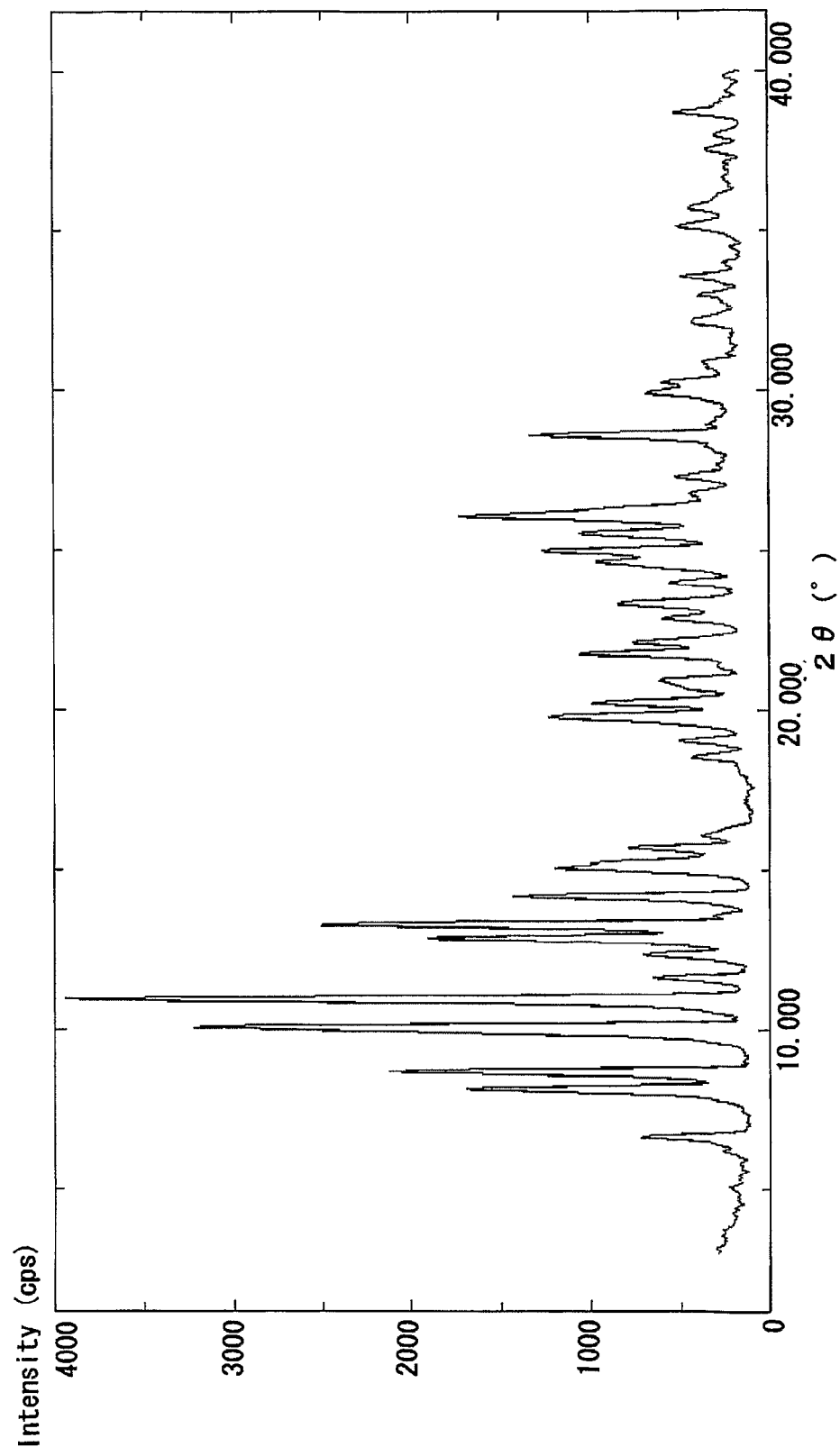
FIG. 2 is the X-ray powder diffraction pattern of the crystals obtained by Example 2.

Monocalcium bis((2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylate)•trihydrate A mixture of (2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylic acid acetone solvate (60 g), ethanol (540 ml) and water (108 ml) was heated to 60° C., and 5% aqueous ammonia (54 ml) was added dropwise thereto with stirring to dissolve the mixture. The solution was stirred at about the same temperature for 30 minutes and, after filtration, the solution was washed with a mixture of ethanol (60 ml) and water (12 ml). The filtrate was combined with the washings to obtain a solution of ammonium (2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylate. The solution was warmed to 75° C., and an aqueous solution of calcium chloride (5.9 g/120 ml) was added dropwise thereto with keeping the temperature almost the same and stirring. The reaction mixture was heated to 78° C., and stirred at about the same temperature for 3 hours and then at 25° C. for 1 hour. Crystals were collected by filtration, washed with ethanol/water (120 ml/120 ml), dried and stored at room temperature to obtain the title compound as colorless crystals (49 g, yield 80.1%). The crystals obtained showed the X-ray powder diffraction pattern as shown in FIG. 2 and have the following representative lattice spacings. Crystallinity was 75%.

3.1 angstrom weak
3.4 angstrom middle
3.5 angstrom weak
3.6 angstrom weak
4.1 angstrom weak
4.4 angstrom weak
4.5 angstrom weak
5.9 angstrom weak
6.2 angstrom middle
6.7 angstrom middle
6.9 angstrom middle
8.1 angstrom strong
8.8 angstrom strong
10.2 angstrom middle
10.9 angstrom middle $^1$H-NMR (300 MHz, DMSO-$d_6$) δ(ppm): 2.17 (3H, s), 3.32 (2H, br), 6.47 (1H, d, J=16 Hz), 6.87 (1H, s), 7.21-7.23 (1H, m), 7.32-7.54 (6H, m), 7.66 (2H, s), 9.65 (1H, brs).

REFERENCE EXAMPLE 8

Ammonium(2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylate

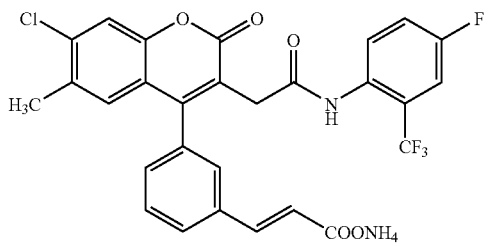

A mixture of (2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylic acid acetone solvate (6.18 g), ethanol (56 ml) and water (11 ml) was heated to 60° C., and 5% aqueous ammonia (6 ml) was added dropwise thereto with stirring to dissolve the mixture. The solution was concentrated under reduced pressure and crystals obtained were dried at 45° C. for 8 hours under reduced pressure to obtain the title compound as colorless crystals (5.20 g, yield 90.1%).

$^1$H-NMR (300 MHz, DMSO-$d_6$) δ(ppm): 2.18 (3H, s), 3.34 (2H, br), 3.80 (4H, brs), 6.46 (1H, d, J=16 Hz), 6.85 (1H, s), 7.25-7.60 (8H, m), 7.76 (1H, d, J=8 Hz), 9.68 (1H, brs).

EXAMPLE 3

(2E)-3-{3-[7-Chloro-3-(2-{[4-fluoro-2-(trifluoromethyl)phenyl]amino}-2-oxoethyl)-6-methyl-2-oxo-2H-chromen-4-yl]phenyl}acrylic acid tris(hydroxymethyl)methylamine salt

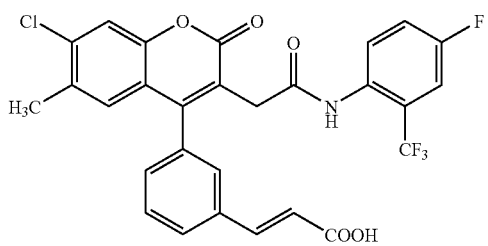

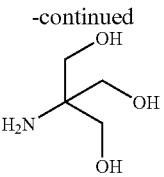

Figure 3:
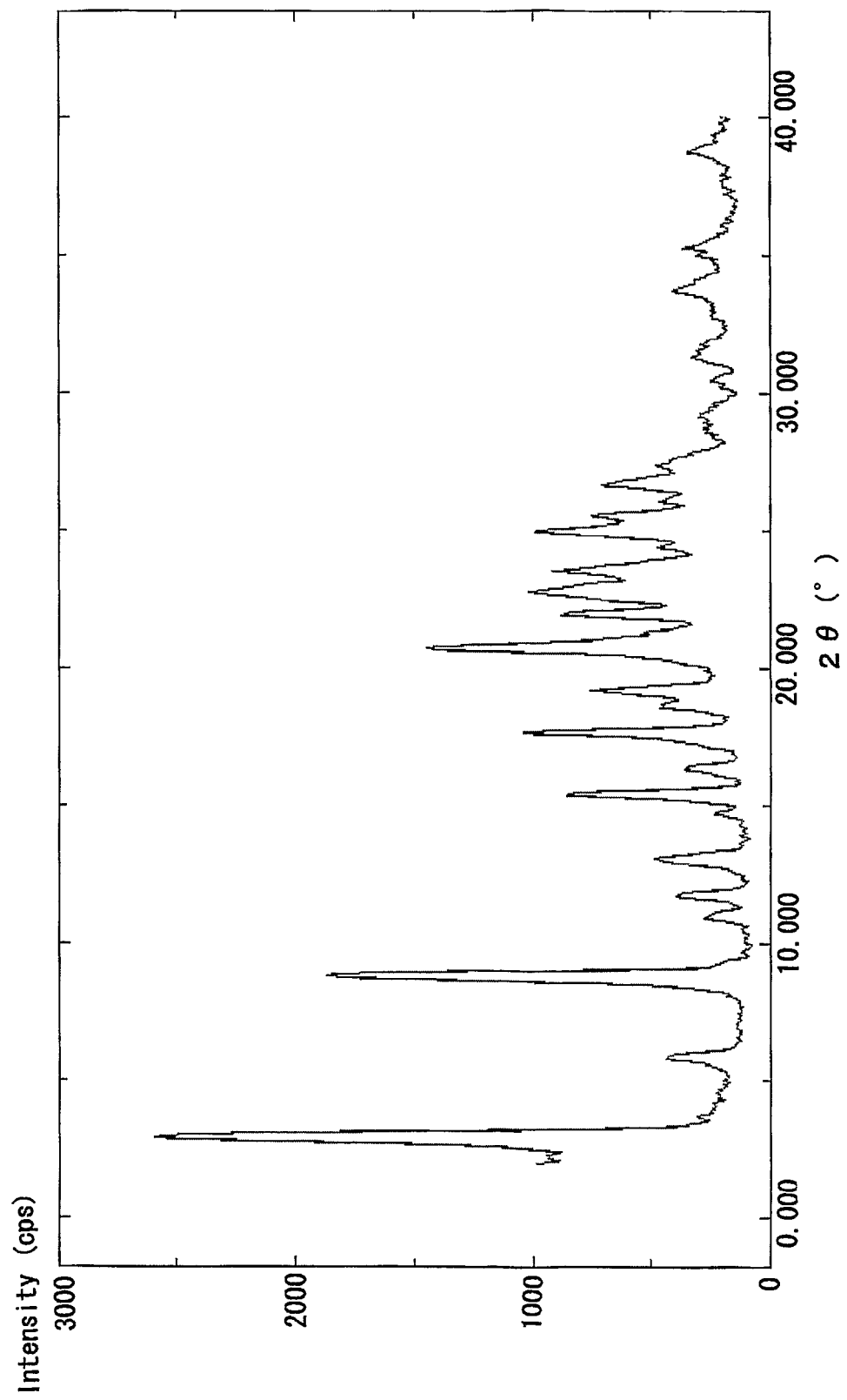
FIG. 3 is the X-ray powder diffraction pattern of the crystals obtained by Example 3.

A mixture of (2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylic acid (10.0 g), tris(hydroxymethyl)methylamine (2.2 g), ethanol (70 ml) and acetonitrile (100 ml) was heated and stirred at 70° C. to dissolve the mixture. Acetonitrile (200 ml) was slowly added to the reaction mixture, and the mixture was stirred at 70° C. for 3 hours, gradually cooled to room temperature, and then stirred at room temperature overnight. Crystals obtained were collected by filtration, washed with acetonitrile, and dried at 60° C. for 8 hours under reduced pressure to obtain the title compound as colorless crystals (10.5 g, yield 86%). The crystals obtained showed the X-ray powder diffraction pattern as shown in FIG. 3 and crystallinity was 64%.

$^1$H-NMR (300 MHz, DMSO-$d_6$) δ(ppm): 2.54 (3H, s), 3.38 (8H, m), 6.52 (1H, d, J=16 Hz), 6.93 (1H, s), 7.3-7.4 (3H, m), 7.5-7.6 (4H, m), 7.71 (1H, s), 7.80 (1H, d, J=7.8 Hz), 9.67 (1H, brs).

EXAMPLE 4

(2E)-3-{3-[7-Chloro-3-(2-{[4-fluoro-2-(trifluoromethyl)phenyl]amino}-2-oxoethyl)-6-methyl-2-oxo-2H-chromen-4-yl]phenyl}acrylic acid-diethanolamine salt

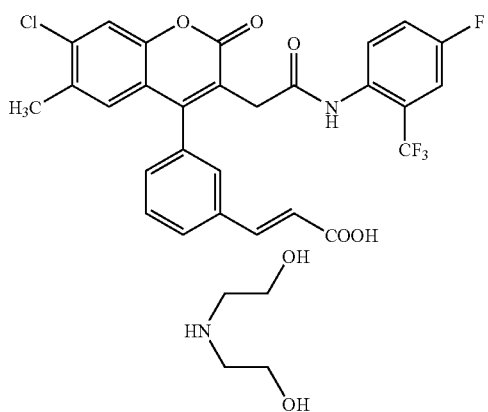

A solution of diethanolamine (0.20 g) in ethanol (20 ml) was added to a solution of (2E)-3-{3-[7-chloro-3-(2-{[4-fluoro-2-(trifluoromethyl)phenyl]amino}-2-oxoethyl)-6-methyl-2-oxo-2H-chromen-4-yl]phenyl}acrylic acid (1.0 g) in a mixture of tetrahydrofuran (30 ml) and ethanol (100 ml), and the mixture was stirred at room temperature for 1 hour. The solvent was evaporated under reduced pressure, and crystals obtained were washed with ethanol, and dried at 60° C. for 8 hours under reduced pressure to obtain the title compound as colorless crystals (0.8 g, yield 67%).

$^1$H-NMR (300 MHz, DMSO-$d_6$) δ(ppm): 2.25 (3H, s), 2.75 (4H, t, J=5.6 Hz), 3.36 (2H, m), 3.54 (4H, t, J=5.6 Hz), 6.54 (1H, d, J=16 Hz), 6.93 (1H, s), 7.30-7.4 (3H, m), 7.5-7.7 (4H, m), 7.71 (1H, s), 7.84 (1H, d, J=7.6 Hz), 9.67(1H, brs).

EXAMPLE 5

Monocalcium bis(3-{3-[7-chloro-3-(2-{[4-fluoro-2-(trifluoromethyl)phenyl]amino}-2-oxoethyl)-6-methyl-2-oxo-2H-chromen-4-yl]phenyl}propionate)

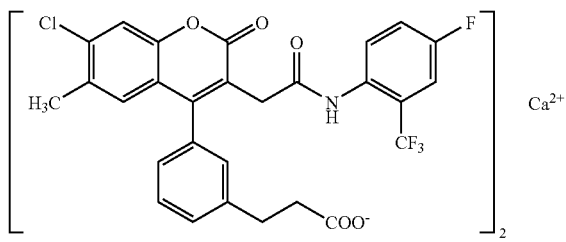

A mixture of 3-{3-[7-chloro-3-(2-{[4-fluoro-2-(trifluoromethyl)phenyl]amino}-2-oxoethyl)-6-methyl-2-oxo-2H-chromen-4-yl]phenyl}propionic acid (100 mg) and acetone (2 ml) was heated to 50° C., and 1N NaOH (0.18 ml) was added dropwise thereto with stirring. The mixture was stirred at 50° C. for 2 hours and at 5° C. for 1 hour, and crystals precipitated were collected by filtration. The crystals were washed successively with cold acetone/water (95/5, 2 ml) and cold acetone (2 ml) to obtain the corresponding sodium salt. A mixture of the sodium salt thus obtained, ethanol (1 ml) and water (0.2 ml) was heated to 50° C. to dissolve the mixture, and a solution of calcium chloride (11 mg) in water (0.2 ml) was added dropwise thereto with stirring at 60° C. After stirring at 60° C. for 2 hours, the mixture was stirred at room temperature overnight. Crystals were collected by filtration, and washed successively with ethanol/water (1/1) and water (10 ml×3) to obtain the title compound as colorless crystals (63 mg, yield 61%).

$^1$H-NMR (300 MHz, DMSO-$d_6$) δ(ppm): 2.20 (3H,s), 2.2-2.4 (2H, m), 2.7-2.9 (2H, m), 3.36 (2H, m), 6.90 (1H, s), 7.06 (1H, d, J=7.2 Hz), 7.15 (1H, s), 7.3-7.7 (5H, m), 7.69 (1H, s), 9.78 (1H, brs).

EXAMPLE 6

Monocalcium bis(3-{3-[6-chloro-3-(2-{[4-fluoro-2-(trifluoromethyl)phenyl]amino}-2-oxoethyl)-7-methyl-2-oxo-2H-chromen-4-yl]phenyl}propionate)

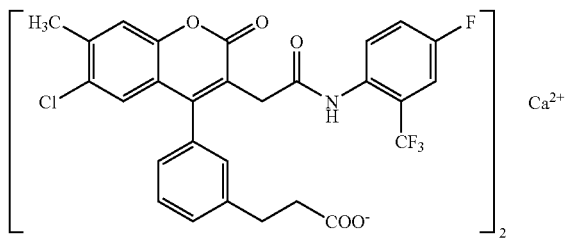

A mixture of 3-{3-[6-chloro-3-(2-{[4-fluoro-2-(trifluoromethyl)phenyl]amino}-2-oxoethyl)-7-methyl-2-oxo-2H-chromen-4-yl]phenyl}propionic acid (100 mg) and acetone (2 ml) was heated to 50° C., and 1N NaOH (0.18 ml) was added dropwise thereto with stirring. The mixture was stirred at 50° C. for 2 hours and at 5° C. for 1 hour, and crystals precipitated were collected by filtration. The crystals were washed successively with cold acetone/water (95/5, 2 ml) and cold acetone (2 ml) to obtain the corresponding sodium salt. A mixture of the sodium salt thus obtained, ethanol (1 ml) and water (0.2 ml) was heated to 50° C. to dissolve the mixture, and a solution of calcium chloride (11 mg) in water (0.2 ml) was added dropwise thereto with stirring at 60° C. After stirring at 60° C. for 2 hours, the mixture was stirred at room temperature overnight. Crystals were collected by filtration, and washed successively with ethanol/water (1/1) and water (10 ml×3) to obtain the title compound as colorless crystals (70 mg, yield 68%).

$^1$H-NMR (300 MHz, DMSO-$d_6$) δ(ppm): 2.2-2.4 (2H, m), 2.40 (3H, s), 2.7-2.9 (2H, m), 3.38 (2H, m), 6.88 (1H, s), 7.09 (1H, d, J=7.2 Hz), 7.18 (1H, s), 7.3-7.6 (6H, m), 9.75 (1H, brs).

EXAMPLE 7

Monocalcium bis(4-{3-[7-chloro-3-(2-{[4-fluoro-2-(trifluoromethyl)phenyl]amino}-2-oxoethyl)-6-methyl-2-oxo-2H-chromen-4-yl]phenyl}butanoate)

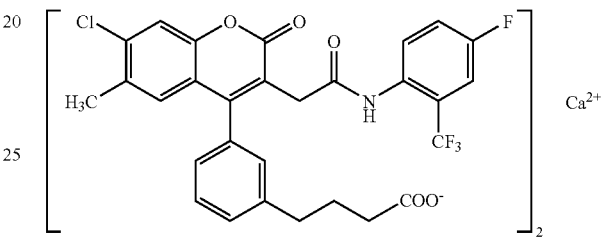

A mixture of 4-{3-[7-chloro-3-(2-{[4-fluoro-2-(trifluoromethyl)phenyl]amino}-2-oxoethyl)-6-methyl-2-oxo-2H-chromen-4-yl]phenyl}butanoic acid (100 mg) and acetone (2 ml) was heated to 50° C., and 1N NaOH (0.18 ml) was added dropwise thereto with stirring. The mixture was stirred at 50° C. for 2 hours, cooled, and concentrated under reduced pressure. The residue was dissolved in a mixture of ethanol (1 ml) and water (0.2 ml) and a solution of calcium chloride (11 mg) in water (0.2 ml) was added dropwise thereto with stirring at 50° C. The mixture was stirred at 60° C. for 2 hours and then at room temperature overnight. Crystals were collected by filtration, washed successively with ethanol/water (1/1) and water (10 ml×3) to obtain the title compound as colorless crystals (89 mg, yield 86%)

$^1$H-NMR (300 MHz, DMSO-$d_6$) δ(ppm): 1.7-1.9 (2H, m), 1.9-2.1 (2H, m), 2.19 (3H, s), 2.5-2.7 (2H, m), 3.36 (2H, m), 6.87 (1H, s), 7.08 (1H, d, J=7.2 Hz), 7.10 (1H, s), 7.3-7.6 (5H, m), 7.64 (1H, s), 9.82 (1H, brs).

EXAMPLE 8

Monocalcium bis((2E)-3-{3-[7-chloro-3-(2-{[2-(trifluoromethyl)phenyl]amino}-2-oxoethyl)-6-methyl-2-oxo-2H-chromen-4-yl]phenyl}acrylate)

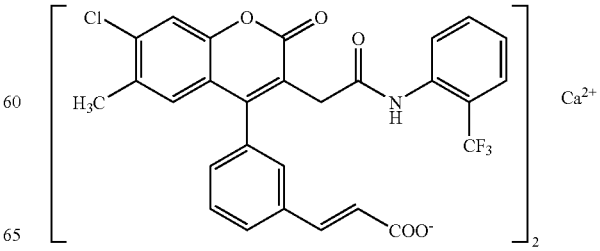

According to the same manner as that described in Example 7, the title compound was obtained (yield 73%).

$^1$H-NMR (300 MHz, DMSO-$d_6$) δ(ppm): 2.20 (3H, s), 3.35 (2H, m), 6.47 (1H, d, J=16 Hz), 7.2-7.8 (10H, m), 9.60 (1H, br).

REFERENCE EXAMPLE 9

4-{3-[7-chloro-3-(2-{[4-fluoro-2-(trifluoromethyl)phenyl]amino}-2-oxoethyl)-7-methyl-2-oxo-2H-chromen-4-yl]phenyl}butanoic acid

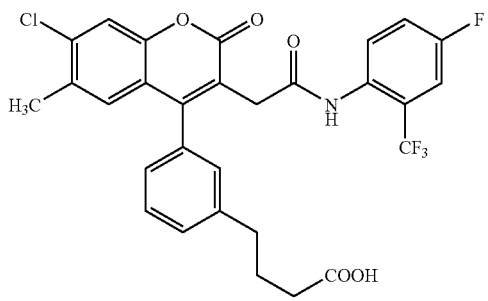

A solution of 0.4N 9-borabicyclo[3.3.1]nonane in tetrahydrofuran (300 ml, 0.12 mol) was added dropwise to a solution of methyl 3-butenoate (12.01 g, 0.12 mol) in tetrahydrofuran (5 ml) at room temperature under nitrogen atmosphere, and the mixture was stirred for 3 hours. This reaction mixture was added dropwise to a solution of 2-[4-(3-bromophenyl)-7-chloro-6-methyl-2-oxo-2H-chromen-3-yl]-N-[4-fluoro-2-(trifluoromethyl)phenyl]acetamide obtained in Reference Example 4 (34.12 g, 0.06 mol), sodium methoxide (9.72 g, 0.18 mol) and (1,1'-bis-(diphenylphosphino)ferrocene)palladium dichloride (9.8 g, 0.012 mol) in tetrahydrofuran (150 ml) at room temperature under nitrogen atmosphere, and the mixture was refluxed for 17 hours. To the reaction mixture was added an aqueous solution of 1N hydrochloric acid, and the mixture was extracted with ethyl acetate. The extract was washed with water and saturated saline, and dried over magnesium sulfate. The extract was concentrated, and roughly purified by silica gel column chromatography to obtain a crude product of methyl 4-{3-[7-chloro-3-(2-{[4-fluoro-2-(trifluoromethyl)phenyl]amino}-2-oxoethyl)-7-methyl-2-oxo-2H-chromen-4-yl]phenyl}butanoate (34.96 g). This was dissolved in a mixed solvent of ethanol (300 ml) and tetrahydrofuran (300 ml), an 2N aqueous solution of sodium hydroxide (118.5 ml, 0.237 mol) was added thereto, and the mixture was stirred at room temperature for 12 hours. The reaction mixture was extracted with water. The extract was washed with diethyl ether, neutralized with 6N hydrochloric acid, and extracted with ethyl acetate. The extract was washed with saturated saline, dried over magnesium sulfate, and concentrated. The residue was purified by column chromatography and then re-crystallized from acetonitrile to obtain the title compound (12.04 g): mp 196° C.

$^1$H-NMR (300 MHz, DMSO-$d_6$) δ(ppm): 1.77-1.89 (2H, m), 2.17-2.28 (5H, m), 2.60-2.72 (2H, m), 3.34 (2H, s), 6.90 (1H, s), 7.12-7.19 (2H, m), 7.33-7.43 (2H, m), 7.47-7.63 (3H, m), 7.68 (1H, s), 9.62 (1H, s), 12.04 (1H, s).

EXAMPLE 9

Monocalcium bis(4-{3-[7-chloro-3-(2-{[4-fluoro-2-(trifluoromethyl)phenyl]amino}-2-oxoethyl)-6-methyl-2-oxo-2H-chromen-4-yl]phenyl}butanoate)

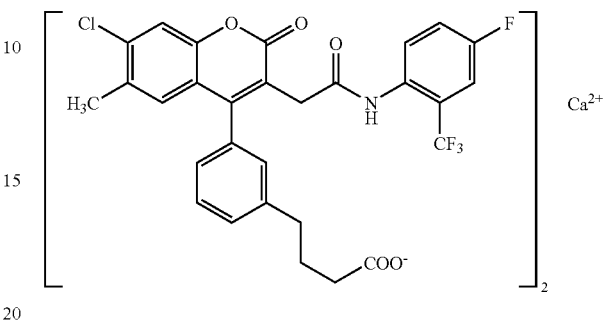

To a solution of 4-{3-[7-chloro-3-(2-{[4-fluoro-2-(trifluoromethyl)phenyl]amino}-2-oxoethyl)-6-methyl-2-oxo-2H-chromen-4-yl]phenyl}butanoic acid obtained in Reference Example 9 (26.7 g, 0.0463 mol) in acetone (534 ml) was added 25% aqueous ammonia (4 ml) at 50° C., and the mixture was stirred at the same temperature for 15 minutes. The reaction mixture was concentrated under reduced pressure and the residue was dissolved in a mixture of acetonitrile (534 ml) and water (107 ml). The reaction mixture was heated to 70° C., and a solution of calcium chloride (3.14 g, 0.0255 mol) in water (107 ml) was slowly added dropwise thereto. The reaction mixture was stirred at 70° C. for 3.5 hours, water (214 ml) was added thereto and the mixture was further stirred at 70° C. for 1 hour and at room temperature for 12 hours. Crystals obtained were collected by filtration, washed with water (100 ml) and dried at 50° C. under reduced pressure to obtain the title compound (26.67 g).

$^1$H-NMR (300 MHz, DMSO-$d_6$) δ(ppm): 1.71-1.85 (2H, m), 2.03 (2H, t, J=7.1 Hz), 2.20 (3H, s), 2.62(2H, t, J=7.2 Hz), 3.30-3.44 (2H, m), 6.88 (1H, s), 7.07-7.16 (2H, m), 7.32-7.41 (2H, m), 7.45 (1H, t, J=7.7 Hz), 7.50-7.61 (2H, m), 7.65 (1H, s), 9.77 (1H, s).

REFERENCE EXAMPLE 10

4-Methoxybenzyl[4-{3-bromophenyl)-7-chloro-6-methyl-2oxo-2H-chromen-4-yl]phenyl}acetate]

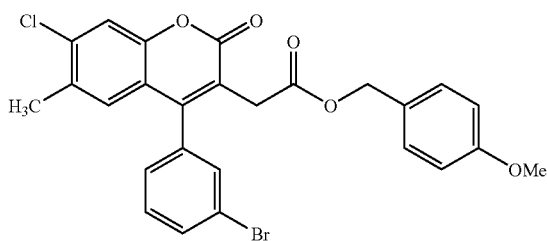

Potassium carbonate (1.52 g) was added to a solution of [4-(3-bromophenyl)-7-chloro-6-methyl-2-oxo-2H-chromen-3-yl]acetic acid obtained in Reference Example 3 (4.08 g) and p-methoxybenzyl chloride (1.63 ml) in DMF (20 ml), and the mixture was stirred at room temperature for 60 hours. The reaction mixture was poured into water and extracted with ethyl acetate. The extract was washed with water, dried over magnesium sulfate, and concentrated to obtain the title compound (4.35 g, 82%).

¹H-NMR (300 MHz, CDCl$_3$) δ(ppm): 2.29 (3H, s), 3.38 (3H, s), 3.81 (3H, s), 5.06 (2H, s), 6.78 (1H, s), 6.88 (2H, ddd, J=8.8 Hz, 2.8 Hz, 2.0 Hz), 7.12-7.17 (1H, m), 7.26 (2H, ddd, J=8.8 Hz, 2.8 Hz, 2.0 Hz), 7.32-7.41 (3H, m), 7.56 (1H, ddd, J=8.8 Hz, 1.8 Hz, 1.2 Hz).

REFERENCE EXAMPLE 11

Ethyl(2E)-3-[3-(7-chloro-3-{2-[(4-methoxybenzoyl)oxy]-2-oxoethyl}-6-methyl-2-oxo-2-chromen-4-yl)phenyl]acrylate

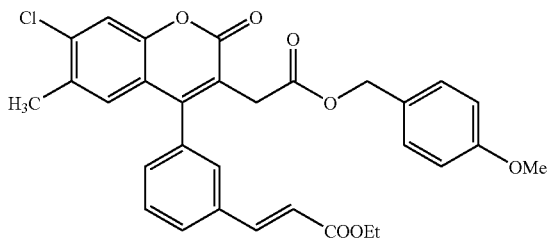

Palladium acetate (850 mg) and triphenylphosphine (2.0 g) were added to a solution of 4-methoxybenzyl[4-(3-bromophenyl)-7-chloro-6-methyl-2-oxo-2H-chromen-3-yl]acetate obtained in Reference Example 10 (20 g), ethyl acrylate (5.1 ml) and triethylamine (6.3 ml) in DMF (100 ml), and the mixture was stirred at 100° C. for 4 hours. The reaction mixture was diluted with water and extracted with ethyl acetate. The extract was washed with water, dried over magnesium sulfate, and concentrated. The residue was purified by column chromatography (developing solvent:ethyl acetate-hexane=1:3) to obtain the title compound as crystals (17 g, 36%).

¹H-NMR (300 MHz, CDCl$_3$) δ(ppm): 1.34 (3H, t, J=7.2 Hz), 2.28 (3H, s), 3.39 (2H, s), 3.80 (3H, s), 4.28 (2H, q, J=7.2 Hz), 5.05 (2H, s), 6.47 (1H, d, J=16.2 Hz), 6.78 (1H, s), 6.87 (2H, d, J=8.7 Hz), 7.20-7.25 (3H, m), 7.38-7.42 (2H, m), 7.51 (1H, t, J=7.8 Hz), 7.64-7.72 (2H, m).

REFERENCE EXAMPLE 12

(7-Chloro-4-{3-[(1E)-3-ethoxy-3-oxo-1-propen-1-yl]phenyl}-6-methyl-2-oxo-2H-chromen-3-yl)acetic acid

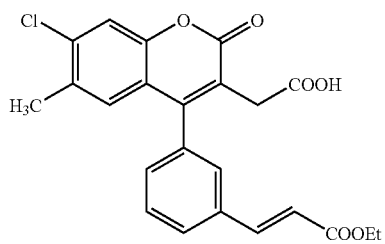

Trifluoroacetic acid (12 ml) was added to a mixture of ethyl (2E)-3-[3-(7-chloro-3-{2-[(4-methoxybenzoyl)oxy]-2-oxoethyl}-6-methyl-2-oxo-2-chromen-4-yl)phenyl]acrylate obtained in Reference Example 11 (2.95 g) and anisole (2 ml), and the mixture was stirred at room temperature for 30 minutes. The solvent was evaporated under reduced pressure, water was added to the residue, and the mixture was extracted with ethyl acetate. The extract was washed with water, dried over magnesium sulfate and concentrated to obtain the title compound as crystals (2.0 g, 87%).

¹H-NMR (300 MHz, CDCl$_3$) δ(ppm):1.33 (3H, t, J=7.2 Hz), 2.28 (3H, s), 3.36 (1H, d, J=16.8 Hz), 3.44 (1H, d, J=16.8 Hz), 4.26 (2H, q, J=7.2 Hz), 6.48 (1H, d, J=13.2 Hz), 6.80 (1H, s), 7.26-7.29 (1H, m), 7.40-7.42 (2H, m), 7.59 (1H, t, J=7.8 Hz), 7.67-7.73 (2H, m).

REFERENCE EXAMPLE 13

N-(5-Fluoro-4-methoxy-2-nitrophenyl)acetamide

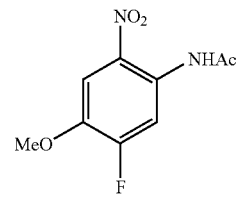

Acetic anhydride (5 ml) was added to 3-fluoro-4-methoxyaniline (5.0 g), and the mixture was stirred for 30 minutes. The reaction mixture was cooled to room temperature, and nitric acid (2.3 ml) was added dropwise thereto. The mixture was stirred for 30 minutes, and water was added thereto. The resulting precipitate was collected and washed with water to obtain the title compound as crystals (5.7 g, 71%).

¹H-NMR (300 MHz, CDCl$_3$) δ(ppm): 2.29 (3H, s), 3.94 (3H, s), 7.80 (1H, d, J=8.4 Hz), 8.66 (1H, d, J=10.5 Hz), 10.39 (1H, brs).

REFERENCE EXAMPLE 14

5-Fluoro-4-methoxy-2-nitroaniline

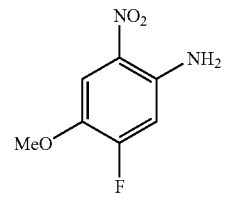

N-(5-Fluoro-4-methoxy-2-nitrophenyl)acetamide obtained in Reference Example 13 (5.7 g) was suspended in ethanol (20 ml), and 6N hydrochloric acid (100 ml) was added thereto. The mixture was refluxed for 30 minutes. The reaction mixture was ice-cooled, and the resulting precipitate was collected and washed with water to obtain the title compound as crystals (4.1 g, 88%).

¹H-NMR (300 MHz, CDCl$_3$) δ(ppm): 3.87 (3H, s), 6.00 (1H, brs), 6.54 (1H, d, J=14.7 Hz), 7.68 (1H, d, J=8.7 Hz).

REFERENCE EXAMPLE 15

1-Bromo-5-fluoro-4-methoxy-2-nitrobenzene

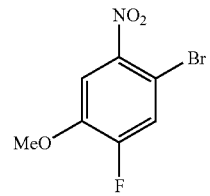

5-Fluoro-4-methoxy-2-nitroaniline obtained in Reference Example 14 (4.1 g) was dissolved in a mixed solvent of water (20 ml) and 1,4-dioxane (10 ml), 48% hydrobromic acid (12 ml) was added to the solution under refluxing, and then the mixture was refluxed for 15 minutes. The reaction mixture was cooled to 0° C., sodium nitrite was added dropwise thereto, and the mixture was stirred at 0° C. for 15 minutes. The resulting mixture was added dropwise to a solution of copper (I) bromide (3.6 g) in a mixture of water (20 ml) and 48% hydrobromic acid (12 ml) at 0° C. The mixture was stirred at 60° C. for 15 minutes, cooled to room temperature, and further stirred for 1 hour. The reaction mixture was extracted with ethyl acetate, and the extract was washed with water, dried over magnesium sulfate and concentrated. The residue was purified by column chromatography (developing solvent:ethyl acetate-hexane=1:8) to obtain the title compound as crystals (5 g, 91%).

$^1$H-NMR (300 MHz, CDCl$_3$) δ(ppm): 3.96 (3H, s), 7.46 (1H, d, J=9.9 Hz), 7.58 (1H, d, J=8.1 Hz).

REFERENCE EXAMPLE 16

1-Fluoro-2-methoxy-4-nitro-5-(trifluoromethyl)benzene

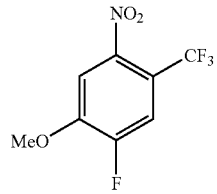

Copper (I) bromide (0.16 g) and FSO$_2$CF$_2$CO$_2$Me (4.2 ml) were added to a solution of 1-bromo-5-fluoro-4-methoxy-2-nitrobenzene obtained in Reference Example 15 (5 g) in DMF (40 ml), and the mixture was stirred at 80° C. overnight under atmosphere. The reaction mixture was cooled to room temperature, an aqueous saturated solution of sodium bicarbonate was added thereto, and the mixture was extracted with ethyl acetate. The extract was washed with water, dried over magnesium sulfate, and concentrated. The residue was purified by column chromatography (developing solvent:ethyl acetate-hexane=1:8) to obtain the title compound as an oily substance (3.1 g, 79%).

$^1$H-NMR (300 MHz, CDCl$_3$) δ(ppm): 4.03 (3H, s), 7.53 (1H, d, J=10.8 Hz), 7.56 (1H, d, J=7.2 Hz).

REFERENCE EXAMPLE 17

2-Fluoro-5-nitro-4-(trifluoromethyl)phenol

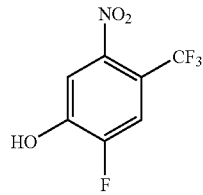

A 1N solution of boron tribromide in dichloromethane (15 ml) was added dropwise to a solution of 1-fluoro-2-methoxy-4-nitro-5-(trifluoromethyl)benzene obtained in Reference Example 16 (1.4 g) in dichloromethane (5 ml) with ice-cooling. After stirring at room temperature overnight, water and 1N hydrochloric acid was added to the reaction mixture. After stirring for 30 minutes, an organic layer was separated, washed with water, dried over magnesium sulfate, and concentrated. The residue was purified by column chromatography (developing solvent:ethyl acetate-hexane=1:3) to obtain the title compound as crystals (0.5 g, 38%).

$^1$H-NMR (300 MHz, CDCl$_3$) δ(ppm): 6.72 (1H, brs), 7.55 (1H, d, J=10.5 Hz), 7.62 (1H, d, J=7.5 Hz).

REFERENCE EXAMPLE 18

Ethyl (2E)-3-{3-[7-chloro-3-(2-{[4-fluoro-5-hydroxy-2-(trifluoromethyl)phenyl]amino}-2-oxoethyl)-6-methyl-2-oxo-2H-chromen-4-yl]phenyl}acrylate

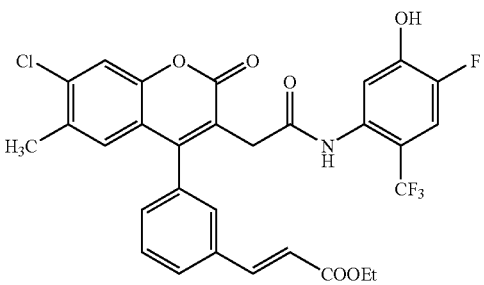

Raney-Ni (0.5 g) was added to a solution of 2-fluoro-5-nitro-4-(trifluoromethyl)phenol obtained in Reference Example 17 (0.5 g) in THF (5 ml), and the mixture was stirred for 2 hours in a hydrogen atmosphere. The catalyst was removed by filtration and the catalyst was washed with THF. The combined filtrate and washings were diluted with THF to obtain a solution of 5-amino-2-fluoro-4-(trifluoromethyl)phenol in THF (50 ml).

DMF (one drop) was added to a solution of (7-chloro-4-{3-[(1E)-3-ethoxy-3-oxo-1-propen-1-yl]phenyl}-6-methyl-2-oxo-2H-chromen-3-yl)acetic acid obtained in Reference Example 12 (800 mg) in THF (20 ml), and oxalyl chloride (0.2 ml) was added dropwise thereto. After stirring for 30 minutes, the reaction mixture was concentrated, the above-mentioned solution of 5-amino-2-fluoro-4-(trifluoromethyl)phenol in THF (50 ml) was added to the residue, and the mixture was stirred overnight. The reaction mixture was concentrated, and the residue was purified by column chromatography (developing solvent:ethyl acetate-hexane=1:3) to obtain the title compound as crystals (0.84 g, 74%).

$^1$H-NMR (300 MHz, CDCl$_3$) δ(ppm): 1.31 (1H, t, J=6.9 Hz), 2.28 (3H, s), 3.42 (1H, d, J=14.7 Hz), 3.62 (1H, d, J=14.7 Hz), 4.23 (2H, q, J=6.9 Hz), 6.48 (1H, d, J=15.6 Hz), 6.84 (1H, s), 7.21 (1H, d, J=10.2 Hz), 7.34 (1H, d, J=7.5 Hz), 7.37 (1H, s), 7.56-7.75 (5H, m), 8.16 (1H, brs), 8.50 (1H, brs).

REFERENCE EXAMPLE 19

(2E)-3-{3-[7-chloro-3-(2-{[4-fluoro-5-hydroxy-2-(trifluoromethyl)phenyl]amino}-2-oxoethyl-6-methyl-2-oxo-2H-chromen-4-yl)phenyl]acrylic acid

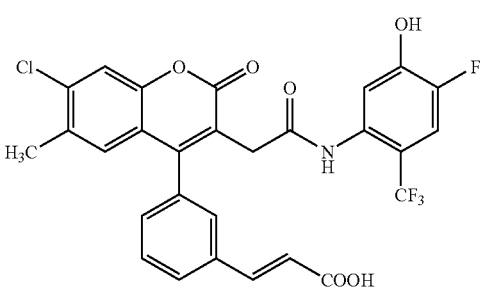

Ethyl (2E)-3-{3-[7-chloro-3-(2-{[4-fluoro-5-hydroxy-2-(trifluoromethyl)phenyl]amino}-2-oxoethyl)-6-methyl-2-oxo-2H-chromen-4-yl]phenyl}acrylate obtained in Reference Example 18 (0.84 g) was dissolved in a mixture of THF (40 ml) and ethanol (40 ml), and 2N aqueous sodium hydroxide solution (5 ml) was added thereto. After stirring for 5 hours, the reaction mixture was concentrated, and 1N hydrochloric acid was added to the residue, and the mixture was extracted with ethyl acetate. The extract was washed with water, dried over magnesium sulfate, and concentrated to obtain the title compound as crystals (0.346 g, 43%).

$^1$H-NMR (300 MHz, CDCl$_3$) δ(ppm): 2.26 (3H, s), 3.34 (2H, m), 6.57 (1H, d, J=16.2 Hz), 6.92 (1H, s), 6.95 (1H, d, J=8.2 Hz), 7.35 (1H, d, J=8.4 Hz), 7.50 (1H, d, J=11.4 Hz), 7.61-7.66 (3H, m), 7.73 (1H, s), 7.92 (1H, d, J=7.8 Hz), 9.52 (1H, brs), 10.94 (1H, brs), 12.41 (1H, brs).

REFERENCE EXAMPLE 20

5-Fluoro-2-nitro-3-(trifluoromethyl)phenol

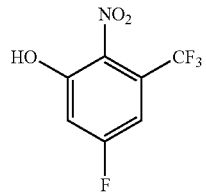

5-Fluoro-3-(trifluoromethyl)phenol (1.27 g) was dissolved in acetic acid (3 ml) and water (1.5 ml), and nitric acid (3.0 ml) was added thereto. The reaction mixture was stirred at 50° C. for 30 minutes. After cooling, water was added to the reaction mixture, and the mixture was extracted with ether. The extract was washed with an aqueous saturated sodium bicarbonate solution and water, dried over magnesium sulfate, and concentrated. The residue was purified by column chromatography (developing solution:ethyl acetate-hexane=1:3) to obtain the title compound as oil (0.33 g, 21%).

$^1$H-NMR (300 MHz, CDCl$_3$) δ(ppm): 7.06 (1H, dd, J=8.7 Hz, 2.7 Hz), 7.15 (1H, m). 25 as an oil: $^1$H-NMR (CDCl$_3$) δ: 6.92 (1H, dd, J=10.5 Hz, 2.7 Hz), 7.02 (1H, m).

REFERENCE EXAMPLE 21

2-Amino-5-fluoro-3-(trifluoromethyl)phenol

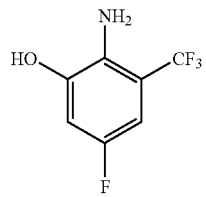

5-Fluoro-2-nitro-3-(trifluoromethyl)phenol obtained in Reference Example 20 was dissolved in ethanol (15 ml), 10% Pd—C (100 mg) was added to the solution, and the mixture was stirred overnight in a hydrogen atmosphere. The catalyst was removed by filtration and the reaction mixture was concentrated to obtain the title compound as oil (0.22 g, 77%).

$^1$H-NMR (300 MHz, CDCl$_3$) δ(ppm): 6.67 (1H, d, J=8.7 Hz), 6.77 (1H, d, J=8.1 Hz).

REFERENCE EXAMPLE 22

Ethyl(2E)-3-{3-[7-chloro-3-(2-{[4-fluoro-2-hydroxy-6-(trifluoromethyl)phenyl]amino}-2-oxoethyl)-6-methyl-2-oxo-2H-chromen-4-yl]phenyl}acrylate

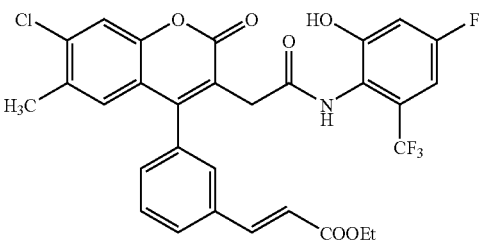

DMF (one drop) was added to a solution of (7-chloro-4-{(3-[(1E)-3-ethoxy-3-oxo-1-propen-1-yl]phenyl)-6-methyl-2-oxo-2H-chromen-3-yl}acetic acid (430 mg) in THF (20 ml), and oxalyl chloride (0.11 ml) was added dropwise thereto. After stirring for 1 hour, the reaction mixture was concentrated. The residue was dissolved in THF (10 ml), 2-amino-5-fluoro-3-(trifluoromethyl)phenol obtained in Reference Example 21 (0.22 g) was added thereto, and the mixture was stirred overnight. Water was added to the reaction mixture, and the mixture was extracted with water. The extract was washed with 1N hydrochloric acid, an aqueous saturated sodium bicarbonate solution and water, dried over magnesium sulfate, and concentrated. The residue was purified by column chromatography (developing solvent:ethyl acetate-hexane=1:3) to obtain the title compound as crystals (0.31 g, 45%).

$^1$H-NMR (300 MHz, CDCl$_3$) δ(ppm): 1.33 (3H, t, J=7.2 Hz), 2.31 (3H, s), 3.48 (1H, d, J=14.7 Hz), 3.54 (1H, d, J=14.7 Hz), 4.27 (2H, q, J=7.2 Hz), 6.51 (1H, d, J=15.9 Hz), 6.88 (1H, s), 6.95 (2H, d, J=8.1 Hz), 7.35 (1H, m), 7.48 (2H, m), 7.61 (1H, t, J=8.1 Hz), 7.72 (2H, m), 8.21 (1H, brs).

REFERENCE EXAMPLE 23

(2E)-3-{3-[7-Chloro-3-(2-{[4-fluoro-2-hydroxy-6-(trifluoromethyl)phenyl]amino}-2-oxoethyl)-6-methyl-2-oxo-2H-chromen-4-yl]phenyl}acrylic acid

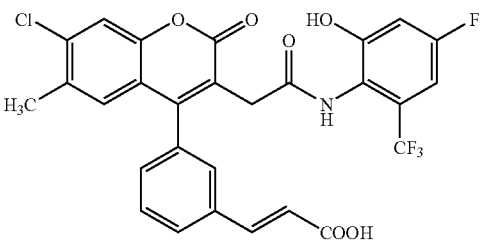

Ethyl (2E)-3-{(3-[7-chloro-3-(2-{[4-fluoro-2-hydroxy-6-(trifluoromethyl)phenyl]amino}-2-oxoethyl)-6-methyl-2-oxo-2H-chromen-4-yl]phenyl}acrylate obtained in Reference Example 22 (0.31 g) was dissolved in a mixture of THF (5 ml) and ethanol (5 ml), and 2N aqueous sodium hydroxide solution (1.5 ml) was added thereto. After stirring for 5 hours, the reaction mixture was concentrated. To the residue was added 1N hydrochloric acid and the mixture was extracted with ethyl acetate. The extract was washed with water, dried over magnesium sulfate and concentrated to obtain the title compound as crystals (0.155 g, 52%).

$^1$H-NMR (300 MHz, CDCl$_3$) δ(ppm): 2.25 (3H, s), 3.33 (2H, m), 6.57 (1H, d, J=16.2 Hz), 6.89-6.99 (3H, m), 7.37 (1H, d, J=7.5 Hz), 7.57-7.69 (4H, m), 7.91 (1H, d, J=7.5 Hz), 9.17 (1H, brs), 10.53 (1H, brs), 12.32 (1H, brs).

In the following Formulation Examples and Experimental Examples, Compounds A to E mean the following compounds.

Compound A: monocalcium bis((2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate) trihydrate, Compound B: (2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate tris(hydroxymethyl)methylamine salt Compound C: (2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate diethanolamine salt Compound D: monocalcium bis(3-[3-[6-chloro-3-(2-[[4-fluoro-2-(trifluoromethyl)phenyl]amino]-2-oxoethyl)-7-methyl-2-oxo-2H-chromen-4-yl]phenyl]propionate)

Compound E: monocalcium bis(4-[3-[7-chloro-3-(2-[[4-fluoro-2-(trifluoromethyl)phenyl]amino]-2-oxoethyl)-6-methyl-2-oxo-2H-chromen-4-yl]phenyl]butanoate

FORMULATION EXAMPLE

A lipid-rich plaque regressing agent or an ACAT inhibitor containing the compound of the present invention as an active ingredient can be produced, for example, by the following formulations.

In the following formulations, as ingredients (additives) other than an active ingredient, products listed in Japanese Pharmacopoeia, Japanese Pharmaceutical Codex or Japanese Pharmaceutical Excipients can be used.

| 1. Capsule | |
|---|---|
| (1) Compound A: | 10 mg |
| (2) Lactose: | 90 mg |
| (3) Microcrystalline Cellulose: | 70 mg |
| (4) Magnesium stearate: | 10 mg |
| One capsule | 180 mg |

(1), (2), (3) and ½ of (4) are mixed and then granulated. To this is added the remainder of (4) and the entire is encapsulated into a gelatin capsule.

| 2. Tablet | |
|---|---|
| (1) Compound A: | 2.705 mg |
| (2) Mannitol: | 438.295 mg |
| (3) Microcrystalline Cellulose: | 90 mg |
| (4) Povidone: | 30 mg |
| (5) Croscarmellose Sodium: | 30 mg |
| (6) Magnesium stearate: | 9 mg |
| (7) Hydroxypropylmethylcellulose: | 16.72 mg |
| (8) Macrogol: | 3.6 mg |
| (9) Titanium Dioxide: | 3.6 mg |
| (10) Ferric Oxide: | 0.08 mg |
| One tablet | 624 mg |

(1), (2), (3) and (4) are granulated. To this granule, (5) and (6) are added and compressed into a tablet. The resulting tablet was coated with the aqueous solution of the mixture of (7), (8), (9) and (10) to give the film coated tablet.

| 3. Injection formulation | |
|---|---|
| (1) Compound A: | 10 mg |
| (2) Inositol: | 100 mg |
| (3) Benzyl alcohol: | 20 mg |
| One ampoule | 130 mg |

(1), (2) and (3) are dissolved in distilled water for injection to make the total volume 2 ml, and charged in an ampoule. All steps are performed aseptically.

| 4. Capsule | |
|---|---|
| (1) Compound B: | 10 mg |
| (2) Lactose: | 90 mg |
| (3) Microcrystalline Cellulose: | 70 mg |
| (4) Magnesium stearate: | 10 mg |
| One capsule | 180 mg |

(1), (2), (3) and ½ of (4) are mixed and then granulated. To this is added the remainder of (4) and the entire is encapsulated into a gelatin capsule.

| 5. Tablet | |
|---|---|
| (1) Compound B: | 2.705 mg |
| (2) Mannitol: | 438.295 mg |
| (3) Microcrystalline Cellulose: | 90 mg |
| (4) Povidone: | 30 mg |
| (5) Croscarmellose Sodium: | 30 mg |
| (6) Magnesium stearate: | 9 mg |
| (7) Hydroxypropylmethylcellulose: | 16.72 mg |
| (8) Macrogol: | 3.6 mg |
| (9) Titanium Dioxide: | 3.6 mg |
| (10) Ferric Oxide: | 0.08 mg |
| One tablet | 624 mg |

(1), (2), (3) and (4) are granulated. To this granule, (5) and (6) are added and compressed into a tablet. The resulting tablet was coated with the aqueous solution of the mixture of (7), (8), (9) and (10) to give the film coated tablet.

| 6. Injection formulation | |
|---|---|
| (1) Compound B: | 10 mg |
| (2) Inositol: | 100 mg |
| (3) Benzyl alcohol: | 20 mg |
| One ampoule | 130 mg |

(1), (2) and (3) are dissolved in distilled water for injection to make the total volume 2 ml, and charged in an ampoule. All steps are performed aseptically.

| 7. Capsule | |
| --- | --- |
| (1) Compound C: | 10 mg |
| (2) Lactose: | 90 mg |
| (3) Microcrystalline Cellulose: | 70 mg |
| (4) Magnesium stearate: | 10 mg |
| One capsule | 180 mg |

(1), (2), (3) and ½ of (4) are mixed and then granulated. To this is added the remainder of (4) and the entire is encapsulated into a gelatin capsule.

| 8. Tablet | |
| --- | --- |
| (1) Compound C: | 2.705 mg |
| (2) Mannitol: | 438.295 mg |
| (3) Microcrystalline Cellulose: | 90 mg |
| (4) Povidone: | 30 mg |
| (5) Croscarmellose Sodium: | 30 mg |
| (6) Magnesium stearate: | 9 mg |
| (7) Hydroxypropylmethylcellulose | 16.72 mg |
| (8) Macrogol: | 3.6 mg |
| (9) Titanium Dioxide: | 3.6 mg |
| (10) Ferric Oxide: | 0.08 mg |
| One tablet | 624 mg |

(1), (2), (3) and (4) are granulated. To this granule, (5) and (6) are added and compressed into a tablet. The resulting tablet was coated with the aqueous solution of the mixture of (7), (8), (9) and (10) to give the film coated tablet.

| 9. Injection formulation | |
| --- | --- |
| (1) Compound C: | 10 mg |
| (2) Inositol: | 100 mg |
| (3) Benzyl alcohol: | 20 mg |
| One ampoule | 130 mg |

(1), (2) and (3) are dissolved in distilled water for injection to make the total volume 2 ml, and charged in an ampoule. All steps are performed aseptically.

| 10. Capsule | |
| --- | --- |
| (1) Compound D: | 10 mg |
| (2) Lactose: | 90 mg |
| (3) Microcrystalline Cellulose: | 70 mg |
| (4) Magnesium stearate: | 10 mg |
| One capsule | 180 mg |

(1), (2), (3) and ½ of (4) are mixed and then granulated. To this is added the remainder of (4) and the entire is encapsulated into a gelatin capsule.

| 11. Tablet | |
| --- | --- |
| (1) Compound D: | 2.705 mg |
| (2) Mannitol: | 438.295 mg |

-continued

| 11. Tablet | |
| --- | --- |
| (3) Microcrystalline Cellulose: | 90 mg |
| (4) Povidone: | 30 mg |
| (5) Croscarmellose Sodium: | 30 mg |
| (6) Magnesium stearate: | 9 mg |
| (7) Hydroxypropylmethylcellulose: | 16.72 mg |
| (8) Macrogol: | 3.6 mg |
| (9) Titanium Dioxide: | 3.6 mg |
| (10) Ferric Oxide: | 0.08 mg |
| One tablet | 624 mg |

(1), (2), (3) and (4) are granulated. To this granule, (5) and (6) are added and compressed into a tablet. The resulting tablet was coated with the aqueous solution of the mixture of (7), (8), (9) and (10) to give the film coated tablet.

| 12. Injection formulation | |
| --- | --- |
| (1) Compound D: | 10 mg |
| (2) Inositol: | 100 mg |
| (3) Benzyl alcohol: | 20 mg |
| One ampoule | 130 mg |

(1), (2) and (3) are dissolved in distilled water for injection to make the total volume 2 ml, and charged in an ampoule. All steps are performed aseptically.

| 13. Capsule | |
| --- | --- |
| (1) Compound E: | 10 mg |
| (2) Lactose: | 90 mg |
| (3) Microcrystalline Cellulose: | 70 mg |
| (4) Magnesium stearate: | 10 mg |
| One capsule | 180 mg |

(1), (2), (3) and ½ of (4) are mixed and then granulated. To this is added the remainder of (4) and the entire is encapsulated into a gelatin capsule.

| 14. Tablet | |
| --- | --- |
| (1) Compound E: | 2.705 mg |
| (2) Mannitol: | 438.295 mg |
| (3) Microcrystalline Cellulose: | 90 mg |
| (4) Povidone: | 30 mg |
| (5) Croscarmellose Sodium: | 30 mg |
| (6) Magnesium stearate: | 9 mg |
| (7) Hydroxypropylmethylcellulose: | 16.72 mg |
| (8) Macrogol: | 3.6 mg |
| (9) Titanium Dioxide: | 3.6 mg |
| (10) Ferric Oxide: | 0.08 mg |
| One tablet | 624 mg |

(1), (2), (3) and (4) are granulated. To this granule, (5) and (6) are added and compressed into a tablet. The resulting tablet was coated with the aqueous solution of the mixture of (7), (8), (9) and (10) to give the film coated tablet.

| 15. Injection formulation | |
|---|---|
| (1) Compound E: | 10 mg |
| (2) Inositol: | 100 mg |
| (3) Benzyl alcohol: | 20 mg |
| One ampoule | 130 mg |

(1), (2) and (3) are dissolved in distilled water for injection to make the total volume 2 ml, and charged in an ampoule. All steps are performed aseptically.

EXPERIMENTAL EXAMPLE 1 (ORAL ABSORBABILITY)

The oral absorbability of the compound of the present invention will be illustrated by the following Experimental Example.

[Method] Male New Zealand white rabbits (n=3) were forced to take Compound A, B or X orally (0.5% suspension in methylcellulose, the dose was 10 mg/kg in terms of Compound X). A blood level of Compound X was measured with time to determine the maximum blood level (Cmax) and time required for reaching the maximum blood level (Tmax). Compound X:(2E)-3-{3-[7-chloro-3-(2-{[4-fluoro-2-(trifluoromethyl)phenyl]amino}-2-oxoethyl)-6-methyl-2-oxo-2H-chromen-4yl]phenyl}acrylic acid described in International Publication WO02/06264.

[Results] The results are shown in Table 1. When Compound A or B was administered orally, a blood level higher than that of oral administration of Compound X was observed.

TABLE 1

| | Compound A | Compound B | Compound X |
|---|---|---|---|
| Cmax (ng/mL) | 132 ± 29 | 150 ± 60 | 17 ± 3 |
| Tmax (h) | 0.67 ± 0.29 | 1.17 ± 0.76 | 1.33 ± 0.58 |

As seen from these results, the compound of the present invention shows excellent oral absorbability.

EXPERIMENTAL EXAMPLE 2 (ACAT INHIBITORY ACTIVITY)

[Preparation of Mouse Abdominal Macrophage Microsome ACAT]

According to the method of Hakamada et al. (Experimental Medicine Supplement vol. 14, No. 12, Circulation Research Protocol, p, 49-52, 1996), an abdominal macrophage was taken from a thioglycolate-stimulated C57BL6J mouse and cultured for 24 hours in a RPMI 1640-25 mM HEPES (pH7.0) medium containing rabbit β-very low density lipoprotein (β-VLDL, 150 μg cholesterol/ml) which had been prepared by the method of Ishii et al. (Ishii I et al., Arterioscler, Thromb., 12, 1139-1145, 1992). The abdominal macrophage was then collected by centrifugation (4° C., 1.000 rpm, 5 minutes) and sonicated. The sonicated liquid was centrifuged (4° C., 5000 rpm, 15 minutes) and then ultracentrifuged (4° C., 50,000 rpm, 90 minutes) to prepare a microsome. The microsome thus obtained was used for measuring ACAT inhibitory activity of a test compound as mouse abdominal macrophage microsome ACAT.

[Method for Measuring ACAT Inhibitory Activity]

A mixture of a test compound, cholesterol-albumin-containing-Tris-HCL buffer (pH 7.5) and mouse abdominal macrophage microsome ACAT was pre-incubated at 37° C. for 10 minutes, and $^3$H-oleyl-CoA was added to react at 37° C. for 20 minutes. A solution composed of chloroform-methyl alcohol-distilled water (2:2:1 v/v) was added to stop the reaction, and produced cholesteryl ester (CE) was extracted with shaking. The extract was subjected to silica gel thin chromatography (petroleum ether:diethyl ether:acetic acid=9:1:0.1 v/v), and the resulting $^3$H-CE fraction was measured with a scintillation counter.

ACAT inhibiting rate was calculated from the proportion based on ACAT activity without a test compound, and an $IC_{50}$ value was calculated as the concentration of a test compound showing ACAT inhibiting rate 50%. As a result, $IC_{50}$ value of the compound A was 1956 nM.

As apparent from the above results, the compound of the present invention has excellent ACAT inhibitory activity, and useful as a novel arteriosclerosis treating agent that results in inhibiting formation of and regressing an arteriosclerotic lesion.

INDUSTRIAL APPLICABILITY

Since the compound of the present invention has excellent lipid-rich plaque regressing activity or/and ACAT inhibitory activity, excellent physicochemical properties and oral absorbability, they are useful as a medicament for preventing or treating, coronary syndrome such as myocardial infarction and unstable angina; peripheral artery occlusion, hyperlipemia, cerebral infarction, cerebral apoplexy, arteriosclerosis, atherosclerosis, Alzheimer's disease, multiple risk syndrome and metabolism syndrome, etc. in a mammal (e.g. mouse, rat, rabbit, dog, cat, cow, pig, monkey, human etc.) or preventing or treating restenosis after PTCA or after stent placement.

The invention claimed is:

1. A compound selected from the group consisting of monocalcium bis((2E)-3-[3-[7-chloro-3-(2-[[4-fluoro-2-(trifluoromethyl)phenyl]amino]-2-oxoethyl)-6-methyl-2-oxo-2H-chromen-4-yl]phenyl]acrylate) and (2E)-3-[3-[7-chloro-3-(2-[[4-fluoro-2-(trifluoromethyl)phenyl]amino]-2-oxoethyl)-6-methyl-2-oxo-2H-chromen-4-yl]phenyl] acrylate tris(hydroxymethyl)methylamine salt, or a hydrate thereof, with the hydration number in the range of monohydrate to tetrahydrate.

2. A pharmaceutical composition comprising the compound according to claim 1 and a pharmaceutically acceptable carrier.

3. The pharmaceutical composition according to claim 2, which is an oral preparation.

* * * * *